(12) United States Patent
Heintzelman et al.

(10) Patent No.: US 7,468,373 B2
(45) Date of Patent: Dec. 23, 2008

(54) ARYLINDENOPYRIDINES AND ARYLINDENOPYRIMIDINES AND RELATED THERAPEUTIC AND PROPHYLACTIC METHODS

(75) Inventors: Geoffrey R. Heintzelman, Annandale, NJ (US); James Lawrence Bullington, Hamilton Square, NJ (US); Kenneth C. Rupert, South Orange, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 434 days.

(21) Appl. No.: 11/170,484

(22) Filed: Jun. 29, 2005

(65) Prior Publication Data

US 2005/0267138 A1      Dec. 1, 2005

Related U.S. Application Data

(60) Division of application No. 10/678,562, filed on Oct. 3, 2003, now abandoned, which is a continuation-in-part of application No. 10/259,139, filed on Sep. 27, 2002, now Pat. No. 6,903,109, which is a continuation-in-part of application No. 10/123,389, filed on Apr. 16, 2002, now Pat. No. 6,958,328.

(51) Int. Cl.
*A61K 31/505* (2006.01)
*C07D 239/00* (2006.01)

(52) U.S. Cl. ........................ 514/267; 544/249
(58) Field of Classification Search ........... 544/249; 514/267
See application file for complete search history.

(56) References Cited

U.S. PATENT DOCUMENTS

| | | | |
|---|---|---|---|
| 6,063,788 A | 5/2000 | Brandes et al. | |
| 6,787,541 B1 | 9/2004 | Gillespie et al. | |
| 6,903,109 B2 | 6/2005 | Heintzelman et al. | |
| 6,958,328 B2 | 10/2005 | Heintzelman et al. | |

FOREIGN PATENT DOCUMENTS

| EP | 0825185 A1 | 2/1998 |
|---|---|---|
| JP | 08240921 A2 | 9/1996 |
| JP | 2001 139556 A | 4/2001 |
| WO | WO 93 08167 A | 4/1993 |
| WO | WO 94/09002 A1 | 4/1994 |
| WO | WO 99/03846 A1 | 1/1999 |
| WO | WO 00/42019 A1 | 7/2000 |
| WO | WO 00/68230 A1 | 11/2000 |
| WO | WO 01/21621 A1 | 3/2001 |
| WO | WO 01 62233 A | 8/2001 |
| WO | WO 02 085894 A | 10/2002 |
| WO | WO 03 088963 A | 10/2003 |

OTHER PUBLICATIONS

Gorlitzer et al., 1997, CAS: 127:331459.*
Watanabe et al., 1996, CAS: 126:13066.*
Kandeel et al., 1987, CAS: 107:77748.*
Burger, et al., 1984, CAS: 101:90866.*
Demerac et al., 1973, CAS: 78:29706.*
PCT International Search Report for Appln No. PCT/US02/11823 dated Aug. 27, 2002.
PCT International Search Report for Appln No. PCT/US02/30825 dated Nov. 25, 2002.
PCT Search Report dated Jan. 3, 2004, for PCT Appl. No. PCT/US03/31471.
Afsah, E.M. et al.: "Introduction of some pharmaceuticially active heterocycles into the benzylic moiety of 2-benzyl-1,3-indandione"; Pharmazie 45 (1990), H.4, pp. 255-257.
Bocker, R.H. et al.: "Oxidation of 4-Aryl-and 4-Alkyl-Substituted 2,6-Dimethyl-3,5-bis(alkoxycarbonyl)-1,4-dihydropyridines by Human Liver Microsomes and Immunochemical Evidence for the Involvement of a Form of Cytochrome P-450"; J. Med. Chem. 1986, 29, pp. 1596-1603.
Bradley, G. et al.: "2,3-Dihydroquinolin-4(1H)-ones. Part I. Halogen-substituted 2,3-Di-hydroquinolin-4(1H)-ones and their 1-(2-Acylethyl) Derivatives"; J. Chem. Soc., Perkin Trans. 1, 1972, pp. 2019-2023.

(Continued)

*Primary Examiner*—Rei-tsang Shiao

(57) ABSTRACT

This invention provides novel arylindenopyridines and arylindenopyrimidines of the formula:

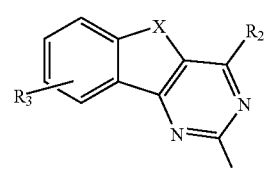

Formula I

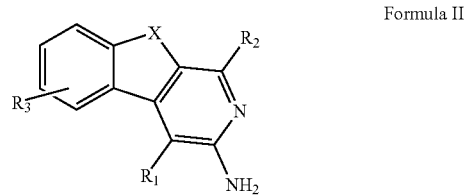

Formula II wherein $R_1$, $R_2$, $R_3$, $R_4$, and X are as defined above, and pharmaceutical compositions comprising same, useful for treating disorders ameliorated by antagonizing adenosine A2a receptors. This invention also provides therapeutic and prophylactic methods using the instant compounds and pharmaceutical compositions.

4 Claims, No Drawings

OTHER PUBLICATIONS

Bullington, J.L. et al.: "The Development of NOvel and Selective p56lck Tyrosine Kinase Inhibitors[1]"; Bioorg. Med. Chem. Lett. 1998, 8, pp. 2489-2494.

Chatterjea, J.N. et al.; "Synthesis in the 4-Azafluorene Group. Part III"; J. Indian Chem. Soc., vol. LV, 1978, pp. 149-153.

Gorlitzer, K. et al.: "Indeo[1,2-b]pyridin-4-yl-amine[3]"; Pharmazie 52 (1997) 7, pp. 504-510.

Jursic, B.S. et al.: "A Simple Preparation of Amides from Acids and Amines by Heating of their Mixture"; Synthetic Comm. 1993, 23, pp. 2761-2770.

Kobayashi, T. et al: "Novel 2-Amino-1,4-dihydropyridine Calcium Antagonists. I. Synthesis and Antihypertensive Effects of 2-Amio-1,4-dihydropyridine Derivatives Having Nitroxyalkoxycarbonyl Groups at 3- and/or 5-Position"; Chem. Pharm. Bull. 1995, 43, pp. 788-796.

Li, L. et al.: "CD3- and CD28-Dependent Induction of PDE7 Required for T Cell Activation"; Science, Feb. 5, 1999, vol. 283, pp. 848-851.

Lusis, V. et al.: "Synthesis and Isomerization of 1H-4,4a,5,9b-Tetrahydroindeno-[1,2-b]pyridines"; Tetrahedron 1991, vol. 47, No. 35, pp. 7429-7436.

Martinez, A. et al.: "Benzyl Derivatives of 2,1,3-Benzo- and Benzothieno[3,2-a]thiadiazine 2,2-Dioxides: First Phosphodiesterase 7 Inhibitors"; J. Med. Chem. 2000, 43, pp. 683-689.

Ogawa, T. et al.: "Synthesis and Configurational Assignment of Methyl 3Nitrooxypropyl 1,4-Dihydro-2,6-dimethyl-4-(3-nitrophenyl)pyridine-3,5-dicarboxylate"; J. Chem. Soc. Perkin Trans. 1 1993, pp. 525-528.

Omuaru, V.O.T.: "Reactions of cyclic anhydrides with aromatic primary amines: Part 3—Synthesis of novel 3-(N-arylcarbamoyl)- and 3-(N-naphthylcarbamoyl)carboxylic acids"; Indian J. of Chem. Sect. B. 1998, 37, pp. 814-816.

Petrow, V. et al.: "New Syntheses of Heterocyclic Compounds. Part X. 4-Azafluorenones", JCS, 1949, pp. 2134-2139.

Reddy, A.S. et al.: "A convenient method for the preparation of hydroxamic acids"; Tetrahedron Letters 41 (2000), pp. 6285-6288.

Rose, U.: "5-Oxo-1,4-dihydroindenopyridines: Calcium Modulators with Partial Calcium Agonistic Activity"; J. Heterocyclic Chem., 27, (1990), pp. 237-242.

Sausin'sh, A. et al.: "Methods for the Synthesis of 4-Pyrazolyl- and 4-Pyridyl-5-Oxo-1,4,5,7-Tetrahydrofuro[3,4-b]Pyridines"; Chem. of Heterocyclic Compounds, vol. 31, No. 7, 1995, pp. 841-846.

Vanden Eynde, J.J. et al.: "Old Reagents, New Results: Aromatization of Hantzsch 1,4-Dihydropyridines awith Manganese Dioxide and 2,3-Dichloro-5,6-dicyano-1,4-benzoquinone."; Tetrahedron vol. 51, No. 23 (1995), pp. 6511-6516.

Vigante, B. et al.: Latv. PSR Zinat. Akad. Vestis, Kin. Ser. 1980, p. 707-175.

Vigante, B.A. et al.: "Infrared Absorption of 4,5-Dihdroindeno[1,2-b]Pyridines"; Chem. Het. Compounds, 25(5) 1989, pp. 524-527.

Weissman, S.A. et al.: "Efficient Synthesis of N-Arylpiperazinones via a Selective Intramolecular Mitsunobu Cyclodehydration"; Tetrehedron Lett. 1998, 39, pp. 7459-7462.

Zandersons, A. et al.: "Synthesis of 5-Oxoindeno[1,2-b]Pyridinium Salts"; Chem. Het. Compounds 22(1), 1986, pp. 73-76.

Zimmer, H. et al.: "Substituted γ-Lactones 28.[1] 3-(Phenylmethylene)-2,4(3H, 5H)-furandiones."; J. Org. Chem. vol. 43, No. 8, 1978, pp. 1541-1544.

Chemical Abstracts, vol. 59, No. 6, Sep. 16, 1963; XP-002211132.

Goerlitzer, K. et al: "Indeno(1,2-b)pyridin-4-yl-amine" Phrmazie, vol. 52, No. 7, 1997, pp. 504-510, XP002211131 ISSN: 0031-7144 cited in the application p. 506; compounds of formulae 8b-10b compounds excluded by proviso.

El-Tawell F. M. A. et. al.: "Synthetic Routes to Fluorenone, Indenopyirdine , 4H-NaphthoA2, 1-Bupyrans and Pyridine Derivaties", Bolettino Chimico Farmaceutico, Societa Editoriale Farmaceutica, Milano, Italy, vol. 140, No. 5, 2001, pp. 306-310, XP009025181, ISSN: 0006-6648 See compound 14.

Goerlitzer K. et al: "IndenoA1, 2-Dupyrimidin-4-yl-Amine IndenoA1, 2Upyrimidin-4-yl-Amines" Pharmazie, Veb Verlag Volk Und Gesundheit. Berlin, DD vol. 52, No. 9, 1997 pp. 670-672, XP001179310, ISSN: 0031-7144 see compounds 3, 6-8 and whole article, especially 2.2.1.

Burger K. et. al. Trifluormethyl-Substituierte Pyrimidine Aus Enaminen Und Trifluoracetonitril Trifluoromethyl-Substituted Pyrimidines From Enamines and Trifluoroacetonitrile Liebigs Annalen Der Chemie, Verlag Chemie GMBH Weinheim, DE, vol. 5, 1984, pp. 991-1002 XP001179309 ISSN: 0170-2041 see compund 18a.

Demerac S. et. al.:"5H-IdenoA1, 2-Dupyrumidin-5-Ones" Australian Journal of Chemistry, XX, XX, vol. 25, 1972, pp. 2651-2657, XP009025111 issn: 0004-9425 see coumpounds 5a-5e and 9-11.

Augustin, M.: Synthese Und Reaktionen Von 2-Abis- (Alklthio)-Methylidenu-Indan-1, 3-Dionen Synthesis and Reactions of 2-Abis-(Alkylthio)-Methlidenu-Indan-1 ,3-Dion, Journal Fuer Praktische Chemie, Wiley WeinHeim, DE, vol. 321, No. 2, 1979, pp. 205-214, XP009025100, ISSN: 1436-9966, see 11b, p. 212 and 11c, p. 213.

N El-Rayyes; "Heterocycles. 14. Sythesis of 5H-Indenopyrumidines" J. Chem. Eng. Data, vol. 32, 1987, pp. 481-483, XP002270517 see formula VII, f,h,j, Va-k.

Kappe C. O. et. al. Sythesis and Reactions of Biginelli-Compounds. Part I Journal of Heterocyclic Chemistry, Heterocorporation Provo, US, Jan. 1989, pp. 55-64, XP002952094, ISSN: 00220152X, see compound 29a.

A. Rosowsky; One Step Sythesis of Nove 2, 4-Diaminopyrumudube Antifolates J. Heterocyclci Chemistry vol. 36, 1999, pp. 723-728, XP002270518 see 20(14).

Kandeel, E.M. et. al.: "Sythnesis of New 1, 2-Dihydro-4-Amino-2-Thioxo-5H-Indeno 1, 2-D Pyrimidin-5-One Derivaties" Pakistan Journal of Scientific and Industrial Research, XX, XX, vol. 29, No. 6, Dec. 1986 pp. 424-426, XP009025187 ISSN: 0030-9885 see V1a, V1b, Va, Vb.

Ascherio, A. et al: "Prospective Study of Caffeine Consumption and Risk of Parkinson's Diesease in Men and Women"; Annals of Neurology, 2001, 50, pp. 56-63.

Chen, J.F. et al.: "Neuroprotection of Caffeine and $A_{2A}$ Adenosine Receptor Inactivation in a Model of Parkinson's Disease"; J. of Neuroscience, 2001, vol. 21 RC143, pp. 1-6.

Chen, W. et al.: "A Colorimetric Assay for Measuring Activation of $G_s$-$G_q$-Coupled Signaling Pathways"; Analytical Biochemsitry, 1995, 226, pp. 349-354.

Ferre, S. et al.: "Stimulation of high-affinity adenosine $A_2$ receptors decreases the affinity of dopamine $D_2$ receptors in rat striatal membranes"; Proceedings of the Nat'l Academy of Sciences of the USA, 1991, 88, pp. 7238-7241.

Fink, J.S. et al.: "Molecular cloning of the rat $A_2$ adenosine receptor: selective co-expression with $D_2$ dopamine receptors in rat striatum"; Molecular Brain Research, 14 (1992), pp. 186-195.

Gessi, S. et al.: "$A_{2A}$ adenosine receptors in human peripheral blood cells"; British J. of Pharm., 2000, 129, pp. 2-11.

Ikeda, K. et al.: "Neuroprotection by adenosine $A_{2A}$ receptor blockade in experimental models of Parkinson's disease"; J. of Neurochemistry, 2002, 80, pp. 262-270.

Impagnatiello, F. et al.: "Adenosine receptors in neurological disorders"; Emerging Therapeutic Targets, 2000, 4, pp. 635-664.

Mally, J. et al.: "Efficacy of an adenosine antagonist, theophylline, in essential tremor: comparison with placebo and propranolol"; J. of the Neurological Sciences, 1995, 132, pp. 129-132.

Rosin, D.L. et al.: "Immunohistochemical Localization of Adenosine $A_{2A}$ Receptors in the Rat Central Nervous System"; The J. of Comparative Neurology, 1998, 401, pp. 163-186.

Salim, H. et al.: "Activation of Adenosine $A_1$ and $A_{2A}$ Receptors Modulates Dopamine $D_2$ Receptor-Induced Responses in Stably Transfected Human Neuroblastoma Cells"; J. of Neurochemistry, 2000, 74, pp. 432-439.

Stiles, G. et al.: "Adenosine Receptors"; The J. of Biological Chem., 1992, vol. 267 No. 10, pp. 6451-6454.

Varani, K. et al.: "Pharmacological and biochemical characterization of purified $A_{2a}$ adenosine receptors in human platelet membranes by [$^3$H]-CGS 21680 binding"; British J. of Pharmacology, 1996, 117, pp. 1693-1701.

Database CHEMCATS Online (Feb. 11, 2001), Interbioscreen Compound Library: 2002:3027027, XP002220645.

Database CHEMCATS 'Online' (Jan. 21, 2002), Ambinter: Exploratory Library: 2002:2845045, 2002: XP002220646.

Database CHEMCATS 'Online' (Jan. 21, 2002), Ambinter: Exploratory Library: 2002:1552297, XP002220647.

Database CHEMCATS 'Online' (Jan. 15, 2002), Bionet Research: 2001:2494341, 2001:2494321, XP002220648.

Database CHEMCATS 'Online' (Jul. 1, 2001), Compounds for Screening: 2001:1603530, XP002220649.

Database CA 'Online' Chemical Abstracts Service, Columbus, OH, US; Kandeel, Ez-El-Din M.: "Synthesis of some new functionalized pyridines, 5-oxoindeno'1, 2-b!pyridines and related compounds of potential pharmaceutical interest" 136:200063 XP002220650 abstract & Mansura Science Bulletin, A; Chemistry (2000), 27(2), 35-49.

Database CA 'Online' Chemical Abstracts Service, Columbus, OH, US; Sausins, A. et al: "Methods of synthesis of 4-(pyridyl)-5-oxo-1, 4, 5, 7-tetrehyrofuor'3, 4-b!pyridines" 124:202067 XP002220651 & Khimiya Geterotsiklicheskikh Soedinenii (1995), (7), 966-72.

Database CA 'Online' Chemical Abstracts Service, Columbus, OH, US; Geies, Ahmed A. et al: "Synthesis of indeno'1, 2-b!pyridines and indeno'1, 2-b!thieno'3, 2-e!pyridines" 128:244011 XP002220652 & Bulletin of the Polish Academy of Sciences, Chemistry (1997), 45(4), 381-390, 2 plates.

Database CA 'Online' Chemical Abstracts Service, Columbus, OH, US; Zandersons, A. et al: "Synthesis of substituted 5-oxoindeno'1, 2-b!pyridinium salts" 105:208733 XP002220654 & Khimiya Geterotsiklicheskikh Soedinenii (1986), (1), 88-90.

Database CA 'Online' Chemical Abstracts Service, Columbus, OH, US; Stankevich, E. et al: "Polynuclear heterocyclic compounds. XIII. New derivatives of 9, 11-dioxo-10-phenyl-11H-indeno'1, 2-b!letrahydroquinoline" 59:35503 XP002220655 & Latvijas Psr Zinatnu Akad. Vestis, Kim. Ser. (1962), (No. 2), 283-6.

Database CA 'Online' Chemical Abstracts Service, Columbus, OH, US; Vanags, G. et al: "Polynuclear heterocyclic compounds. VI. 4, 6 -Diphenyl—2, 3—(CO)—benzoylenepyridine" 58:14816 XP002220656 & Zh. Obshch. Khim. (1962), 32, 1151-9.

Database CA 'Online' Chemical Abstracts Service, Columbus, OH, Vigante, B. et al: "Ethyl esters of 1, 4-dihydropyridine-3, 5-di- and 2-methyl-4-aryl-5oxo-4, 5 dihydro-1H-indeno'1, 2-b!pyridine-3-carbothionic acids" 101:6372 XP002220657 & Khim. Geterotsikl. Soedin. (1984), (2), 210-16.

Database CA 'Online' Chemical Abstracts Service, Columbus, OH, Vigante, B. et al: "Infrared absorption of 4, 5-dihydorindeno'1, 2-b!pyridines" 112:97907 XP002220658 & Khimiya Geterotsiklicheskikh Soedinenii (1989), (5), 629-32.

Database CA 'Online' Chemical Abstracts Service, Columbus, OH, Zandersons, A. et al: "Synthesis of substituted 5-oxoindeno'1, 2-b!pyridinium salts" 105:208733 XP002220659 & Khimiya Geterotsiklicheskikh Soedinenii (1986), (1), 88-90.

Database CA 'Online' Chemical Abstracts Service, Columbus, OH, Vigante, B. et al: "Synthesis and properties of 5-oxo-1, 4-dihydroindeno'1,2-b pyridine-3-casbothiolic acid esters" 95:7009 XP002220660 & Latv. Psr Zinat. Akad. Vestis, Kim. Ser. (1980) (6), 707-16.

Database CA 'Online' Chemical Abstracts Service, Columbus, OH, US; Lusis V. et al.: "Synthesis and isomerization of 1H-4, 4a, 5, 9b-tetrahydroindeno'1, 2-b!pyridines" 116:20903 XP002220653 & Tetrahedron (1991), 47(35), 7429-36.

Database CA 'Online' Chemical Abstracts Service, Columbus, OH, Mucsenietce, D. et al: "Reduction and basic hydrolysis of 5-oxoindeno'1, 2-b!pyridinium salts" 107:236463 XP002220661 & Khimiya Geterotsiklicheskikh Soedinenii (1987), (1), 86-9.

Database CA 'Online' Chemical Abstracts Service, Columbus, OH, Zandersons, A. et al: "Synthesis of substituted 5-oxoindeno'1, 2-b!pyridinium salts" 105:208733 XP002220662 & Khimiya Geterotsiklicheskikh Soedinenii (1986), (1), 88-90.

Database CHEMCATS 'Online' (Jul. 9, 2002) Interchim Intermediats: 2002:2525250 and other XP002220663.

Database CHEMCATS 'Online' (Jul. 9, 2002) Interchim Intermediats: 2002:2403473,-3487,-3488,-3489 and 2002:2548348 XP002220664.

Database CHEMCATS 'Online' (Jul. 9, 2002) Interchim Intermediats: 2002:3011492 to 2002:3011513 XP002220665.

Sengupta, et al., "2,4-Diaminopyrimidines from Dicyandiamide. IV. Condensation with Bicyclic Aromatic Ketones", Journal of Organic Chemistry, vol. 37, No. 9 (1972) pp. 1323-1328 (Accession No. 1972:419601/Document No. 77:19601).

Bello, K., et al. "Near-Infrared Absorbing Methine Dyes Based on Cicyanovinyl Derivatives of Indane-1,3-dione", J. Chem. Soc. 1987, p. 815.

Buckle, D., et al. "Antiallergic Activity of 2-Nitroidan-1,3-diones", J. Med. Chem. 1973, p. 1334.

Okawa, T, et al. "Pyridol[2,3-yrimidine Derivatives: Synthesis via the Intermolecular Aza-Wittig Reaction/Heterocyclization and the Crystal Structure", Synthesis, 1988, p. 1467.

Xing, Y., et al. "Deoxygenation of 7-Oxabicyclo[2.2.2]hepta-1,5-diene Systems to Substituted Benzenes by Titanium Tetrachlorid-Lithium Aluminum Hydride", J. Org. Chem. 1982, p. 140.

Cannon, J. G., "Analog Design", Burger's Medicinal Chemistry and Drug Discovery, Fifth Edition vol. 1, p. 783 (1995).

* cited by examiner

ARYLINDENOPYRIDINES AND ARYLINDENOPYRIMIDINES AND RELATED THERAPEUTIC AND PROPHYLACTIC METHODS

CROSS-REFERENCE TO RELATED APPLICATIONS

This application is a divisional of application Ser. No. 10/678,562 filed on Oct. 3, 2003 now abandoned which is a continuation-in-part of application Ser. No. 10/259,139, filed on Sep. 27, 2002 now U.S. Pat. No. 6,903,109, which is a continuation-in-part of application Ser. No. 10/123,389, filed on Apr. 16, 2002 now U.S. Pat. No. 6,958,328, all of which are incorporated herein by reference.

FIELD OF THE INVENTION

This invention relates to novel arylindenopyridines and arylindenopyrimidines and their therapeutic and prophylactic uses. Disorders treated and/or prevented using these compounds include neurodegenerative and movement disorders ameliorated by antagonizing Adenosine A2a receptors.

BACKGROUND OF THE INVENTION

Adenosine A2a Receptors

Adenosine is a purine nucleotide produced by all metabolically active cells within the body. Adenosine exerts its effects via four subtypes of cell-surface receptors (A1, A2a, A2b and A3), which belong to the G protein coupled receptor superfamily (Stiles, G. L. Journal of Biological Chemistry, 1992, 267, 6451). A1 and A3 couple to inhibitory G protein, while A2a and A2b couple to stimulatory G protein. A2a receptors are mainly found in the brain, both in neurons and glial cells (highest level in the striatum and nucleus accumbens, moderate to high level in olfactory tubercle, hypothalamus, and hippocampus etc. regions) (Rosin, D. L.; Robeva, A.; Woodard, R. L.; Guyenet, P. G.; Linden, J. Journal of Comparative Neurology, 1998, 401, 163).

In peripheral tissues, A2a receptors are found in platelets, neutrophils, vascular smooth muscle and endothelium (Gessi, S.; Varani, K.; Merighi, S.; Ongini, E.; Borea, P. A. British Journal of Pharmacology, 2000, 129, 2). The striatum is the main brain region for the regulation of motor activity, particularly through its innervation from dopaminergic neurons originating in the substantia nigra. The striatum is the major target of the dopaminergic neuron degeneration in patients with Parkinson's Disease (PD). Within the striatum, A2a receptors are co-localized with dopamine D2 receptors, suggesting an important site for the integration of adenosine and dopamine signaling in the brain (Fink, J. S.; Weaver, D. R.; Rivkees, S. A.; Peterfreund, R. A.; Pollack, A. E.; Adler, E. M.; Reppert, S. M. Brain Research Molecular Brain Research, 1992, 14, 186).

Neurochemical studies have shown that activation of A2a receptors reduces the binding affinity of D2 agonist to their receptors. This D2R and A2aR receptor-receptor interaction has been demonstrated in striatal membrane preparations of rats (Ferre, S.; von Euler, G.; Johansson, B.; Fredholm, B. B.; Fuxe, K. Proceedings of the National Academy of Sciences of the United States of America, 1991, 88, 7238) as well as in fibroblast cell lines after transfected with A2aR and D2R cDNAs (Salim, H.; Ferre, S.; Dalal, A.; Peterfreund, R. A.; Fuxe, K.; Vincent, J. D.; Lledo, P. M. Journal of Neurochemistry, 2000, 74, 432). In vivo, pharmacological blockade of A2a receptors using A2a antagonist leads to beneficial effects in dopaminergic neurotoxin MPTP(1-methyl-4-pheny-1,2,3,6-tetrahydropyridine)-induced PD in various species, including mice, rats, and monkeys (Ikeda, K.; Kurokawa, M.; Aoyama, S.; Kuwana, Y. Journal of Neurochemistry, 2002, 80, 262). Furthermore, A2a knockout mice with genetic blockade of A2a function have been found to be less sensitive to motor impairment and neurochemical changes when they were exposed to neurotoxin MPTP (Chen, J. F.; Xu, K.; Petzer, J. P.; Staal, R.; Xu, Y. H.; Beilstein, M.; Sonsalla, P. K.; Castagnoli, K.; Castagnoli, N., Jr.; Schwarzschild, M. A. Journal of Neuroscience, 2001, 21, RC143).

In humans, the adenosine receptor antagonist theophylline has been found to produce beneficial effects in PD patients (Mally, J.; Stone, T. W. Journal of the Neurological Sciences, 1995, 132, 129). Consistently, recent epidemiological study has shown that high caffeine consumption makes people less likely to develop PD (Ascherio, A.; Zhang, S. M.; Hernan, M. A.; Kawachi, I.; Colditz, G. A.; Speizer, F. E.; Willett, W. C. Annals of Neurology, 2001, 50, 56). In summary, adenosine A2a receptor blockers may provide a new class of antiparkinsonian agents (Impagnatiello, F.; Bastia, E.; Ongini, E.; Monopoli, A. Emerging Therapeutic Targets, 2000, 4, 635).

SUMMARY OF THE INVENTION

This invention provides a compound having the structure of Formula I or II

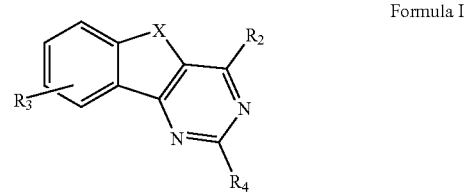

Formula I

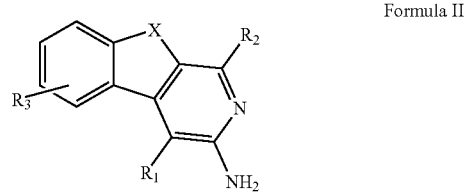

Formula II or a pharmaceutically acceptable salt thereof, wherein
(a) $R_1$ is selected from the group consisting of
  (i)-$COR_5$, wherein $R_5$ is selected from H, optionally substituted $C_{1-8}$ straight or branched chain alkyl, optionally substituted aryl and optionally substituted arylalkyl;
   wherein the substituents on the alkyl, aryl and arylalkyl group are selected from $C_{1-8}$ alkoxy, phenylacetyloxy, hydroxy, halogen, p-tosyloxy, mesyloxy, amino, cyano, carboalkoxy, or $NR_7R_8$ wherein $R_7$ and $R_8$ are independently selected from the group consisting of hydrogen, $C_{1-8}$ straight or branched chain alkyl, $C_{3-7}$ cycloalkyl, benzyl, aryl, or heteroaryl or $NR_7R_8$ taken together form a heterocycle or heteroaryl;
  (ii) $COOR_5$, wherein $R_5$ is as defined above;
  (ii) cyano;
  (iii) —$CONR_9R_{10}$ wherein $R_9$ and $R_{10}$ are independently selected from H, $C_{1-8}$ straight or branched chain alkyl, $C_{3-7}$ cycloalkyl, trifluoromethyl, hydroxy, alkoxy, acyl, alkylcarbonyl, carboxyl, arylalkyl, aryl, heteroaryl and heterocyclyl;

wherein the alkyl, cycloalkyl, alkoxy, acyl, alkylcarbonyl, carboxyl, arylalkyl, aryl, heteroaryl and heterocyclyl groups may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, amino, alkoxy or arylalkyl, or $R_9$ and $R_{10}$ taken together with the nitrogen to which they are attached form a heterocycle or heteroaryl group;

(v) optionally substituted $C_{1-8}$ straight or branched chain alkyl;

wherein the substituents on the alkyl, group are selected from $C_{1-8}$ alkoxy, phenylacetyloxy, hydroxy, halogen, p-tosyloxy, mesyloxy, amino, cyano, carboalkoxy, carboxyl, aryl, heterocyclyl, heteroaryl, sulfonyl, thiol, alkylthio, or $NR_7R_8$ wherein $R_7$ and $R_8$ are as defined above;

(b) $R_2$ is selected from the group consisting of optionally substituted alkyl, optionally substituted aryl, optionally substituted heteroaryl, optionally substituted heterocyclyl and optionally substituted $C_{3-7}$ cycloalkyl, $C_{1-8}$ alkoxy, aryloxy, $C_{1-8}$ alkylsulfonyl, arylsulfonyl, arylthio, $C_{1-8}$ alkylthio, or —$NR_{24}R_{25}$ wherein $R_{24}$ and $R_{25}$ are independently selected from H, $C_{1-8}$ straight or branched chain alkyl, arylalkyl, $C_{3-7}$ cycloalkyl, carboxyalkyl, aryl, heteroaryl, and heterocyclyl or $R_{24}$ and $R_{25}$ taken together with the nitrogen form a heteroaryl or heterocyclyl group, (c) $R_3$ is from one to four groups independently selected from the group consisting of:

hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl, heteroaryl, and heterocyclyl, —$NR_{11}R_{12}$, wherein $R_{11}$ and $R_{12}$ are independently selected from H, $C_{1-8}$ straight or branched chain alkyl, arylalkyl, $C_{3-7}$ cycloalkyl, carboxyalkyl, aryl, heteroaryl, and heterocyclyl or $R_{10}$ and $R_{11}$ taken together with the nitrogen form a heteroaryl or heterocyclyl group, —$NR_{13}COR_{14}$, wherein $R_{13}$ is selected from hydrogen or alkyl and $R_{14}$ is selected from hydrogen, alkyl, substituted alkyl, $C_{1-3}$ alkoxyl, carboxyalkyl, aryl, arylalkyl, heteroaryl, heterocyclyl, $R_{15}R_{16}N(CH_2)_p$—, or $R_{15}R_{16}NCO(CH_2)_p$—, wherein $R_{15}$ and $R_{16}$ are independently selected from H, OH, alkyl, and alkoxy, and p is an integer from 1-6, wherein the alkyl group may be substituted with carboxyl, alkyl, aryl, substituted aryl, heterocyclyl, substituted heterocyclyl, heteroaryl, substituted heteroaryl, hydroxamic acid, sulfonamide, sulfonyl, hydroxy, thiol, alkoxy or arylalkyl, or $R_{13}$ and $R_{14}$ taken together with the carbonyl form a carbonyl containing heterocyclyl group;

(d) $R_4$ is selected from the group consisting of hydrogen, $C_{1-6}$ straight or branched chain alkyl, benzyl wherein the alkyl and benzyl groups are optionally substituted with one or more groups selected from $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, amino, $NR_{17}R_{18}$, aryl and heteroaryl, —$OR_{17}$, and —$NR_{17}R_{18}$, wherein $R_{17}$ and $R_{18}$ are independently selected from hydrogen, and optionally substituted $C_{1-6}$ alkyl or aryl; and (e) X is selected from C=S, C=O; $CH_2$, CHOH, $CHOR_{19}$; or $CHNR_{20}OR_{21}$ where $R_{19}$, $R_{20}$, and $R_{21}$ are selected from optionally substituted $C_{1-8}$ straight of branched chain alkyl, wherein the substituents on the alkyl group are selected from $C_{1-8}$ alkoxy, hydroxy, halogen, amino, cyano, or $NR_{22}R_{23}$ wherein $R_{22}$ and $R_{23}$ are independently selected from the group consisting of hydrogen, $C_{1-8}$ straight or branched chain alkyl, $C_{3-7}$ cycloalkyl, benzyl, aryl, heteroaryl, or $NR_{22}R_{23}$ taken together from a heterocycle or heteroaryl;

with the proviso that in a compound of Formula II when $R_1$ is a cyano, then $R_2$ is not phenyl.

This invention also provides a pharmaceutical composition comprising the instant compound and a pharmaceutically acceptable carrier.

This invention further provides a method of treating a subject having a condition ameliorated by antagonizing Adenosine A2a receptors, which comprises administering to the subject a therapeutically effective dose of the instant pharmaceutical composition.

This invention further provides a method of preventing a disorder ameliorated by antagonizing Adenosine A2a receptors in a subject, comprising of administering to the subject a prophylactically effective dose of the compound of claim 1 either preceding or subsequent to an event anticipated to cause a disorder ameliorated by antagonizing Adenosine A2a receptors in the subject.

DETAILED DESCRIPTION OF THE INVENTION

Compounds of Formula I are potent small molecule antagonists of the Adenosine A2a receptors that have demonstrated potency for the antagonism of Adenosine A2a, A1, and A3 receptors.

Preferred embodiments for $R_1$ are $COOR_5$ wherein $R_5$ is an optionally substituted $C_{1-8}$ straight or branched chain alkyl. Preferably the alkyl chain is substituted with a dialkylamino group.

Preferred embodiments for $R_2$ are optionally substituted heteroaryl and optionally substituted aryl. Preferably, $R_2$ is an optionally substituted furan.

Preferred substituents for $R_3$ include hydrogen, halo, hydroxy, amino, trifluoromethyl, alkoxy, hydroxyalkyl chains, and aminoalkyl chains, Preferred substituents for $R_4$ include $NH_2$ and alkylamino.

In a preferred embodiment, the compound is selected from the group of compounds shown in Tables 1 and 2 hereinafter.

More preferably, the compound is selected from the following compounds:

The compound of claim 1, formula I, wherein $R_4$ is amino.
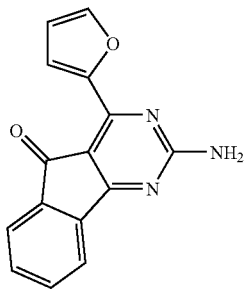
2-amino-4-furan-2-yl-indeno[1,2-d]pyrimidin-5-one
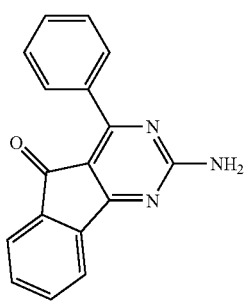
2-amino-4-phenyl-indeno[1,2-d]pyrimidin-5-one
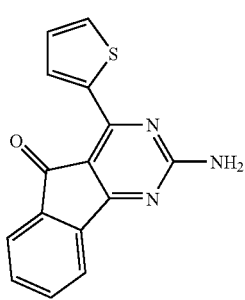
2-amino-4-thiophen-2-yl-indeno[1,2-d]pyrimidin-5-one
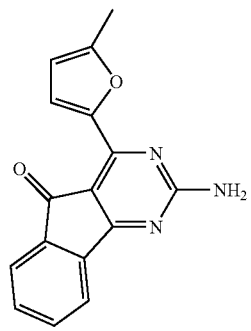
2-amino-4-(5-methyl-furan-2-yl)-indeno[1,2-d]pyrimidin-5-one
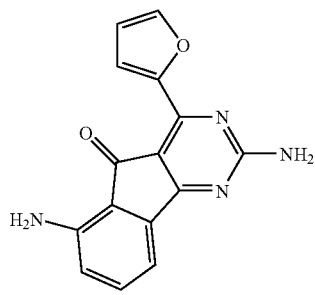
2,6-diamino-4-furan-2-yl-indeno[1,2-d]pyrimidin-5-one
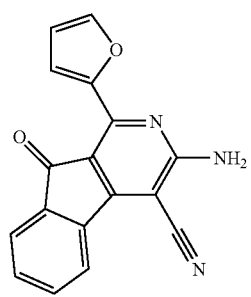

7

9H-indeno[2,1-c]pyridine-4-carbonitrile, 3-amino-1-furan-2-yl-9-oxo-

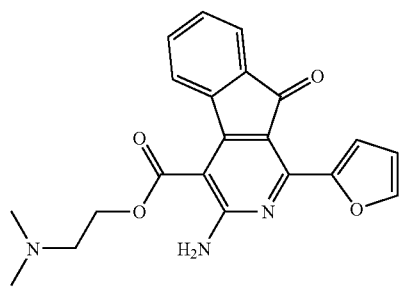

9H-indeno[2,1-c]pyridine-4-carboxylic acid, 3-amino-1-furan-2-yl-9-oxo-, 2-dimethylamino-ethyl ester

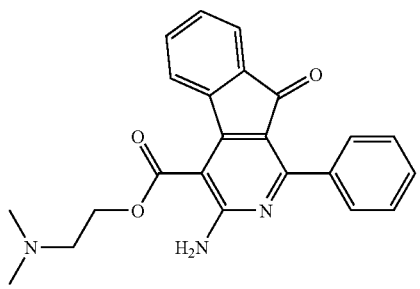

9H-indeno[2,1-c]pyridine-4-carboxylic acid, 3-amino-1-phenyl-9-oxo-, 2-dimethylamino-ethyl ester

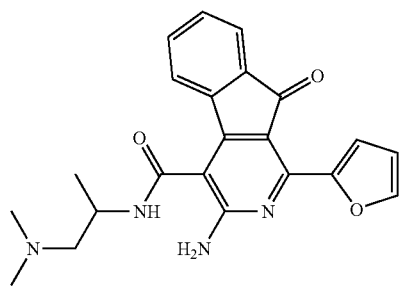

8

9H-indeno[2,1-c]pyridine-4-carboxylic acid, 3-amino1-furan-2-yl-9-oxo-, (2-dimethylamino-1-methyl-ethyl)-amide

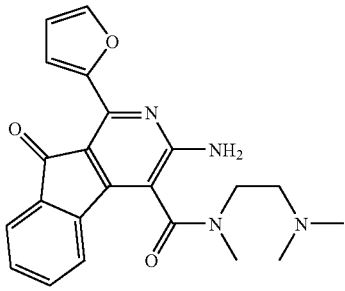

9H-indeno[2,1-c]pyridine-4-carboxylic acid, 3-amino-1-furan-2-yl-9-oxo-, (2-dimethylamino-ethyl)-methyl-amide

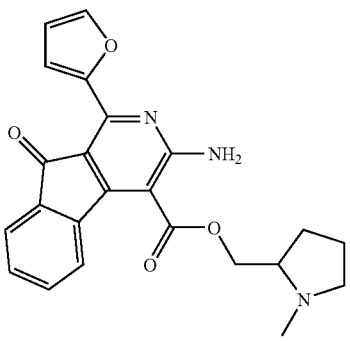

9H-indeno[2,1-c]pyridine-4-carboxylic acid, 3-amino-1-furan-2-yl-9-oxo-, 1-methyl-pyrrolidin-2-ylmethyl ester The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention also provides a pharmaceutical composition comprising the instant compound and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by antagonizing Adenosine A2a receptors, which comprises administering to the subject a therapeutically effective dose of the instant pharmaceutical composition.

In one embodiment, the disorder is a neurodegenerative or movement disorder. Examples of disorders treatable by the instant pharmaceutical composition include, without limitation, Parkinson's Disease, Huntington's Disease, Multiple System Atrophy, Corticobasal Degeneration, Alzheimer's Disease, and Senile Dementia.

In one preferred embodiment, the disorder is Parkinson's disease.

As used herein, the term "subject" includes, without limitation, any animal or artificially modified animal having a disorder ameliorated by antagonizing adenosine A2a receptors. In a preferred embodiment, the subject is a human.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate, and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.001 mg/kg of body weight to about 200 mg/kg of body weight of the instant pharmaceutical composition. In another embodiment, the therapeutically and/or prophylactically effective dose is a dose sufficient to deliver from about 0.05 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0 µg/kg/min to about 10 mg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

Definitions and Nomenclature

Unless otherwise noted, under standard nomenclature used throughout this disclosure the terminal portion of the designated side chain is described first, followed by the adjacent functionality toward the point of attachment.

As used herein, the following chemical terms shall have the meanings as set forth in the following paragraphs: "independently", when in reference to chemical substituents, shall mean that when more than one substituent exists, the substituents may be the same or different.

"Alkyl" shall mean straight, cyclic and branched-chain alkyl. Unless otherwise stated, the alkyl group will contain 1-20 carbon atoms. Unless otherwise stated, the alkyl group may be optionally substituted with one or more groups such as halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, carboxamide, hydroxamic acid, sulfonamide, sulfonyl, thiol, aryl, aryl($c_1$-$C_8$)alkyl, heterocyclyl, and heteroaryl.

"Alkoxy" shall mean —O-alkyl and unless otherwise stated, it will have 1-8 carbon atoms.

The term "bioisostere" is defined as "groups or molecules which have chemical and physical properties producing broadly similar biological properties." (Burger's Medicinal Chemistry and Drug Discovery, M. E. Wolff, ed. Fifth Edition, Vol. 1, 1995, Pg. 785).

"Halogen" shall mean fluorine, chlorine, bromine or iodine; "PH" or "Ph" shall mean phenyl; "Ac" shall mean acyl; "Bn" shall mean benzyl.

The term "acyl" as used herein, whether used alone or as part of a substituent group, means an organic radical having 2 to 6 carbon atoms (branched or straight chain) derived from an organic acid by removal of the hydroxyl group. The term "Ac" as used herein, whether used alone or as part of a substituent group, means acetyl.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl.

Whether used alone or as part of a substituent group, "heteroaryl" refers to a cyclic, fully unsaturated radical having from five to ten ring atoms of which one ring atom is selected from S, O, and N; 0-2 ring atoms are additional heteroatoms independently selected from S, O, and N; and the remaining ring atoms are carbon. The radical may be joined to the rest of the molecule via any of the ring atoms. Exemplary heteroaryl groups include, for example, pyridinyl, pyrazinyl, pyrimidinyl, pyridazinyl, pyrroyl, pyrazolyl, imidazolyl, thiazolyl, oxazolyl, isoxazolyl, thiadiazolyl, triazolyl, triazinyl, oxadiazolyl, thienyl, furanyl, quinolinyl, isoquinolinyl, indolyl, isothiazolyl, 2-oxazepinyl, azepinyl, N-oxo-pyridyl, 1-dioxothienyl, benzothiazolyl, benzoxazolyl, benzothienyl, quinolinyl-N-oxide, benzimidazolyl, benzopyranyl, benzisothiazolyl, benzisoxazolyl, benzodiazinyl, benzofurazanyl, benzothiopyranyl, indazolyl, indolizinyl, benzofuryl, chromonyl, coumarinyl, cinnolinyl, quinoxalinyl, indazolyl, pyrrolopyridinyl, furopyridinyl (such as furo[2,3-c]pyridinyl, furo[3,2-b]pyridinyl, or furo[2,3-b]pyridinyl), imidazopyridinyl (such as imidazo[4,5-b]pyridinyl or imidazo[4,5-c]pyridinyl), naphthyridinyl, phthalazinyl, purinyl, pyridopyridyl, quinazolinyl, thienofuryl, thienopyridyl, thienothienyl, and furyl. The heteroaryl group may be substituted by independent replacement of 1 to 5 of the hydrogen atoms thereon with halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, or carboxamide. Heteroaryl may be substituted with a mono-oxo to give for example a 4-oxo-1H-quinoline.

The terms "heterocycle," "heterocyclic," and "heterocyclo" refer to an optionally substituted, fully or partially saturated cyclic group which is, for example, a 4- to 7-membered monocyclic, 7- to 11-membered bicyclic, or 10- to 15-membered tricyclic ring system, which has at least one heteroatom in at least one carbon atom containing ring. Each ring of the heterocyclic group containing a heteroatom may have 1, 2, or 3 heteroatoms selected from nitrogen atoms, oxygen atoms, and sulfur atoms, where the nitrogen and sulfur heteroatoms may also optionally be oxidized. The nitrogen atoms may optionally be quaternized. The heterocyclic group may be attached at any heteroatom or carbon atom.

Exemplary monocyclic heterocyclic groups include pyrrolidinyl; oxetanyl; pyrazolinyl; imidazolinyl; imidazolidinyl; oxazolyl; oxazolidinyl; isoxazolinyl; thiazolidinyl; isothiazolidinyl; tetrahydrofuryl; piperidinyl; piperazinyl; 2-oxopiperazinyl; 2-oxopiperidinyl; 2-oxopyrrolidinyl; 4-piperidonyl; tetrahydropyranyl; tetrahydrothiopyranyl; tetrahydrothiopyranyl sulfone; morpholinyl; thiomorpholinyl; thiomorpholinyl sulfoxide; thiomorpholinyl sulfone; 1,3-dioxolane; dioxanyl; thietanyl; thiiranyl; and the like. Exemplary bicyclic heterocyclic groups include quinuclidinyl; tetrahydroisoquinolinyl; dihydroisoindolyl; dihydroquinazolinyl (such as 3,4-dihydro-4-oxo-quinazolinyl); dihydrobenzofuryl; dihydrobenzothienyl; dihydrobenzothiopyranyl; dihydrobenzothiopyranyl sulfone; dihydrobenzopyranyl; indolinyl; isochromanyl; isoindolinyl; piperonyl; tetrahydroquinolinyl; and the like.

Substituted aryl, substituted heteroaryl, and substituted heterocycle may also be substituted with a second substituted-aryl, a second substituted-heteroaryl, or a second substituted-heterocycle to give, for example, a 4-pyrazol-1-yl-phenyl or 4-pyridin-2-yl-phenyl.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

I. General Synthetic Schemes

Representative compounds of the present invention can be synthesized in accordance with the general synthetic methods described below and illustrated in the following general schemes. The products of some schemes can be used as intermediates to produce more than one of the instant compounds. The choice of intermediates to be used to produce subsequent compounds of the present invention is a matter of discretion that is well within the capabilities of those skilled in the art.

Procedures described in Schemes 1 to 7, wherein $R_{3a}$, $R_{3b}$, $R_{3c}$, and $R_{3d}$ are independently any $R_3$ group, and $R_1$, $R_2$, $R_3$, and $R_4$ are as described above, can be used to prepare compounds of the invention.

The substituted pyrimidines 1 can be prepared as shown in Scheme 1. The indanone or indandione 2 or the indene ester 3 can be condensed with an aldehyde to yield the substituted benzylidenes 4 (Bullington, J. L; Cameron, J. C.; Davis, J. E.; Dodd, J. H.; Harris, C. A.; Henry, J. R.; Pellegrino-Gensey, J. L.; Rupert, K. C.; Siekierka, J. J. Bioorg. Med. Chem. Lett. 1998, 8, 2489; Petrow, V.; Saper, J.; Sturgeon, B. J. Chem. Soc. 1949, 2134). This is then condensed with guanidine carbonate to form the indenopyrimidine 1.

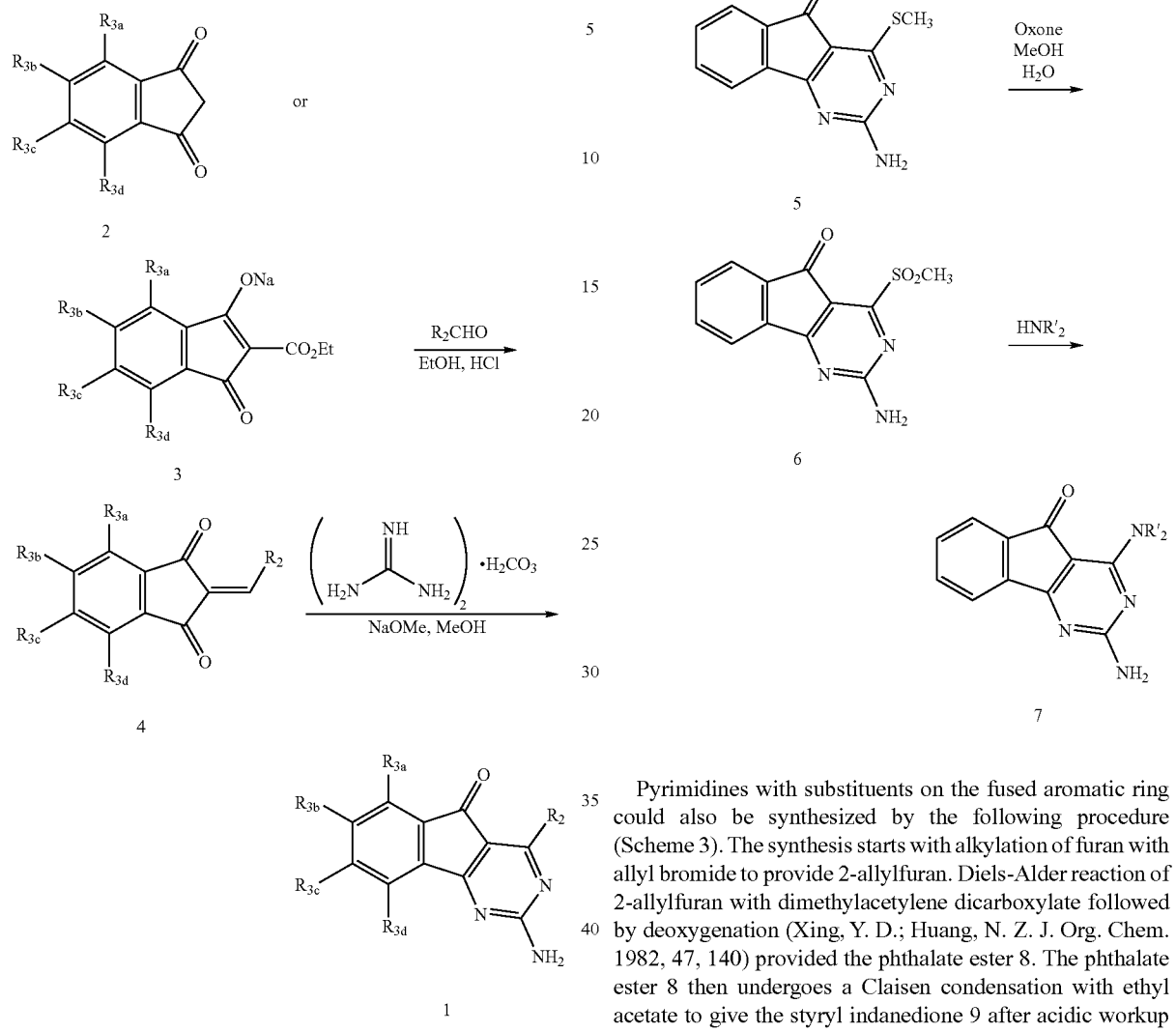

Alternatively, the pyrimidine compounds can be prepared as shown in Scheme 2. Sulfone 6 can be prepared by oxidation of the thiol ether 5 and the desired amines 7 can be obtained by treatment of the sulfone with aromatic amines.

Pyrimidines with substituents on the fused aromatic ring could also be synthesized by the following procedure (Scheme 3). The synthesis starts with alkylation of furan with allyl bromide to provide 2-allylfuran. Diels-Alder reaction of 2-allylfuran with dimethylacetylene dicarboxylate followed by deoxygenation (Xing, Y. D.; Huang, N. Z. J. Org. Chem. 1982, 47, 140) provided the phthalate ester 8. The phthalate ester 8 then undergoes a Claisen condensation with ethyl acetate to give the styryl indanedione 9 after acidic workup (Buckle, D. R.; Morgan, N. J.; Ross, J. W.; Smith, H.; Spicer, B. A. J. Med. Chem. 1973, 16, 1334). The indanedione 9 is then converted to the dimethylketene dithioacetal 10 using carbon disulfide in the presence of KF. Addition of Grignard reagents to the dithioacetal 10 and subsequent reaction with guanidine provides the pyrimidines 11 as a mixture of isomers;

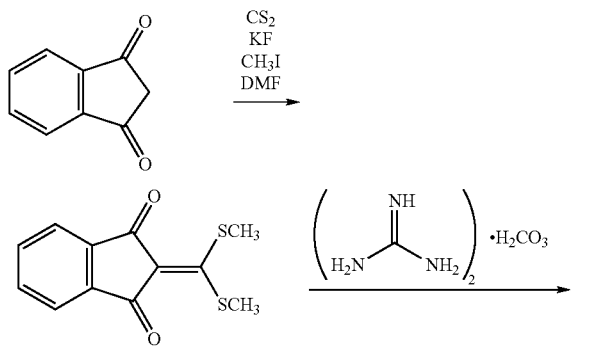

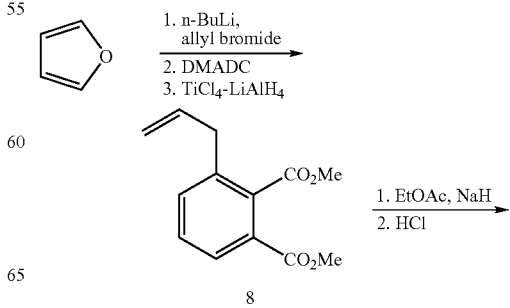

-continued

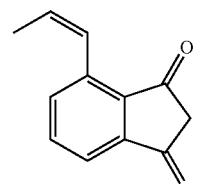
9

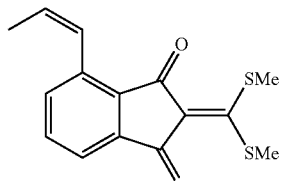
10

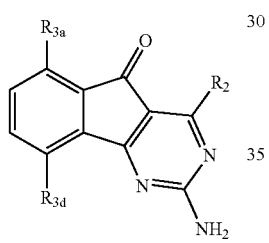
11

R$_{3a}$, R$_{3d}$ = CHCHCH$_3$, H

-continued

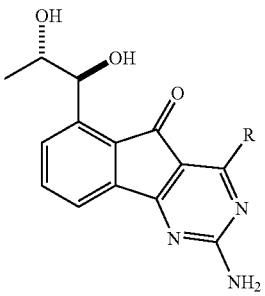
12

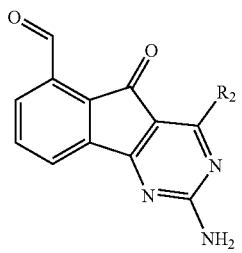
13

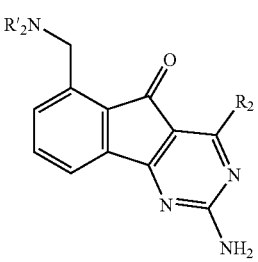
14

Dihydroxylation and oxidation give the aromatic aldehydes 13 that can be reductively aminated to provide amines 14. The other isomer can be treated in a similar manner.

Scheme 4

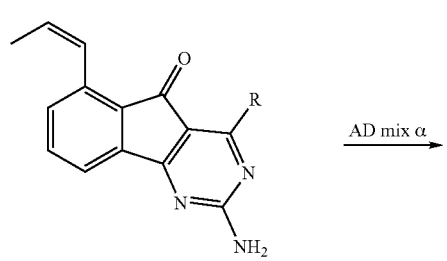

3-Dicyanovinylindan-1-one (15) (Scheme 5) was obtained using the published procedure (Bello, K. A.; Cheng, L.; Griffiths, J. J. Chem. Soc., Perkin Trans. II 1987, 815). Reaction of 3-dicyanovinylindan-1-one with an aldehyde in the presence of ammonium hydroxide produced dihydropyridines 16 (El-Taweel, F. M. A.; Sofan, M. A.; E.-Maati, T. M. A.; Elagamey, A. A. Boll. Chim. Farmac. 2001, 140, 306). These compounds were then oxidized to the corresponding pyridines 17 using chromium trioxide in refluxing acetic acid.

Scheme 5

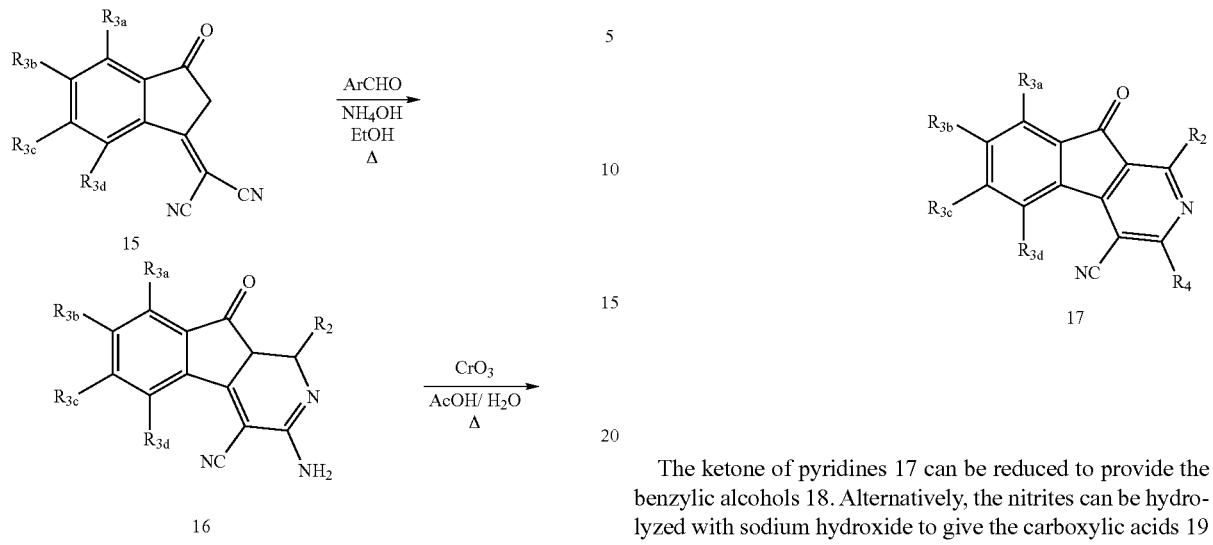

The ketone of pyridines 17 can be reduced to provide the benzylic alcohols 18. Alternatively, the nitriles can be hydrolyzed with sodium hydroxide to give the carboxylic acids 19 (Scheme 6).

Scheme 6

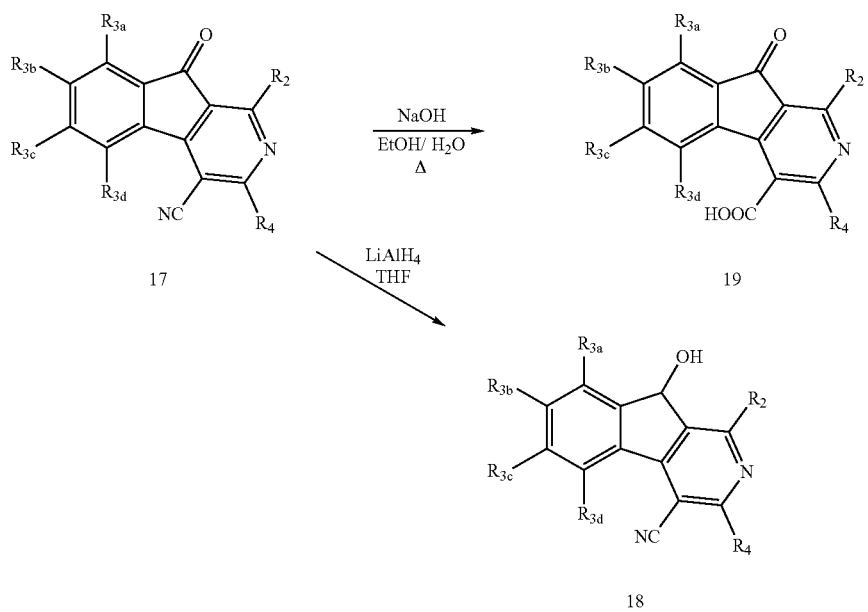

The acids can then be converted to carboxylic esters 20 or amides 21 using a variety of methods. In general, the esters 20 are obtained by treatment with silver carbonate followed by an alkyl chloride or by coupling with diethylphosphoryl cyanide (DEPC) and the appropriate alcohol (Okawa, T.; Toda, M.; Eguchi, S.; Kakehi, A. Synthesis 1998, 1467). The amides 21 are obtained by coupling the carboxylic acid with the appropriate amine in the presence of DEPC or 1-(3-dimethylaminopropyl)-3-ethylcarbodiimide hydrochloride (EDCl). Esters 20 can also be obtained by first reacting the carboxylic acids 19 with a dibromoalkane followed by displacement of the terminal bromide with an amine (Scheme 7).

Scheme 7

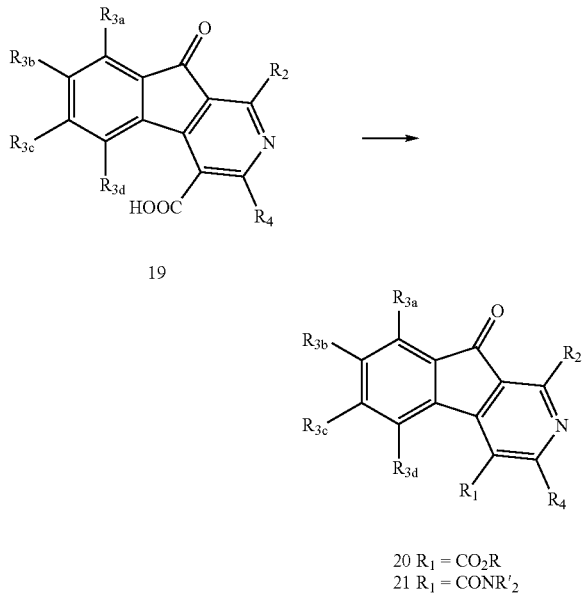

II. Specific Compound Syntheses

Specific compounds which are representative of this invention can be prepared as per the following examples. No attempt has been made to optimize the yields obtained in these reactions. Based on the following, however, one skilled in the art would know how to increase yields through routine variations in reaction times, temperatures, solvents and/or reagents.

The products of certain syntheses can be used as intermediates to produce more than one of the instant compounds. In those cases, the choice of intermediates to be used to produce compounds of the present invention is a matter of discretion that is well within the capabilities of those skilled in the art.

EXAMPLE 1

Synthesis of Benzylidene 4

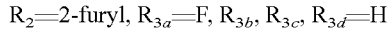

A mixture of 3 (3.0 g, 11.69 mmol) and 2-furaldehyde (1.17 g, 12.17 mmol) in 75 mL of ethanol and 3 mL of concentrated hydrogen chloride was allowed to stir at reflux for 16 hours. The reaction was then cooled to room temperature, and the resulting precipitate was filtered off, washed with ethanol, diethyl ether, and air dried to afford 1.27 g (45%) of product.

EXAMPLE 2

Synthesis of Indenopyrimidine 1

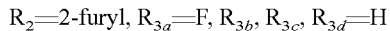

A mixture of 4 (0.5 g, 2.06 mmol), guanidine carbonate (0.93 g, 5.16 mmol), and 20.6 mL of 0.5 M sodium methoxide in methanol was stirred at reflux for 16 hours. The reaction mixture was cooled to room temperature, and diluted with water. The resulting precipitate was collected, washed with water, ethanol, diethyl ether, and then dried. Crude material was then purified over silica gel to afford 0.024 g (4%) of product. MS m/z282.0 (M+H).

EXAMPLE 3

Synthesis of 2-Amino-4-methanesulfonyl-indeno[1,2-d]pyrimidin-5-one

To a suspension of 5 (Augustin, M.; Groth, C.; Kristen, H.; Peseke, K.; Wiechmann, C. J. Prakt. Chem. 1979, 321, 205) (1.97 g, 8.10 mmol) in MeOH (150 mL) was added a solution of oxone (14.94 g, 24.3 mmol) in $H_2O$ (100 mL). The mixture was stirred at room temperature overnight then diluted with cold $H_2O$ (500 mL), made basic with $K_2CO_3$ and filtered. The product was washed with water and ether to give 0.88 g (40%) of sulfone 6. MS m/z297.9 (M+Na).

EXAMPLE 4

Synthesis of Aminopyrimidine 7

A mixture of sulfone 6 (0.20 g, 0.73 mmol) and aniline (0.20 g, 2.19 mmol) in N-methylpyrrolidinone (3.5 mL) was heated to 100° C. for 90 minutes. After cooling to room temperature, the mixture was diluted with EtOAc (100 mL), washed with brine (2×75 mL) and water (2×75 mL), and dried over $Na_2SO_4$. After filtration and concentration in vacuo, the residue was purified by column chromatography eluting with 0-50% EtOAc in hexane to yield 0.0883 g (42%) of product 7. MS m/z 289.0 (M+H).

EXAMPLE 5

Synthesis of Phthalate Ester 8

A 1.37 M hexanes solution of n-BuLi (53.6 mL, 73.4 mmol) was added to a cold, −78° C., THF solution (100 mL) of furan (5.3 mL, 73.4 mmol) and the reaction was then warmed to 0° C. After 1.25 h at 0° C. neat allyl bromide (7.9 mL, 91.8 mmol) was added in one portion. After 1 h at 0° C., saturated aqueous $NH_4Cl$ was added and the layers were separated. The aqueous phase was extracted with EtOAc and the combined organics were washed with water and brine, dried over $Na_2SO_4$, and concentrated to give 4.6 g (58%) of 2-allylfuran which was used without further purification.

The crude allyl furan (4.6 g, 42.6 mmol) and dimethylacetylene dicarboxylate (5.2 mL, 42.6 mmol) were heated to 90° C. in a sealed tube without solvent. After 6 h at 90° C. the material was cooled and purified by column chromatography eluting with 25% EtOAc in hexanes to give 5.8 g (54%) of the oxabicycle as a yellow oil. MS m/z 251 (M+H).

Tetrahydrofuran (60 mL) was added dropwise to neat $TiCl_4$ (16.5 mL, 150.8 mmol) at 0° C. A 1.0 M THF solution of $LiAlH_4$ (60.3 mL, 60.3 mmol) was added dropwise, changing the color of the suspension from yellow to a dark green or black suspension. Triethylamine (2.9 mL, 20.9 mmol) was added and the mixture was refluxed at 75-80° C. After 45 min, the solution was cooled to rt and a THF solution (23 mL) of the oxabicycle (5.8 g, 23.2 mmol) was added to the dark solution. After 2.5 h at rt, the solution was poured into a 20% aq. $K_2CO_3$ solution (200 mL) and the resulting suspension was filtered. The precipitate was washed several times with $CH_2Cl_2$ and the filtrate layers were separated. The aqueous phase was extracted with $CH_2Cl_2$ and the combined organics were washed with water and brine, dried over $Na_2SO_4$, concentrated, and purified by column chromatography eluting with 25% EtOAc in hexanes to give 3.5 g (64%) of the phthalate ester 8 as a yellow oil. MS m/z 235 (M+H).

EXAMPLE 6

Synthesis of Indanedione 9

A 60% dispersion of sodium hydride in mineral oil (641 mg, 16.0 mmol) was added to an EtOAc solution (3.5 mL) of the phthalate ester 8 (2.5 g, 10.7 mmol), and the resulting slurry was refluxed. After 1 h the solution became viscous so an additional 7.5 mL of EtOAc was added. After 4 h at reflux the suspension was cooled to rt and filtered to give a yellow solid. This solid was added portionwise to a solution of HCl (25 mL water and 5 mL conc. HCl) at 80° C. The suspension was heated for an additional 30 min at 80° C., cooled to rt, and filtered to give 1.2 g (60%) of the indanedione 9 as a yellow solid. MS m/z 187 (M+H).

EXAMPLE 7

Synthesis of Dimethylketene Dithioacetal 10

Solid potassium fluoride (7.5 g, 129.1 mmol) was added to a 0° C. solution of indanedione 9 (1.2 g, 6.5 mmol) and $CS_2$ (0.47 mL, 7.8 mmol) in DMF (10 mL). The cold bath was removed and after 30 min neat iodomethane (1.00 mL, 16.3 mmol) was added. After 5 h at rt, the suspension was diluted with EtOAc and then washed with water and brine. The organic layer was dried over $Na_2SO_4$, concentrated, and purified by column chromatography eluting with 20% EtOAc in hexanes to give 1.4 g (75%) of the dimethylketene dithioacetal 10 as a yellow solid. MS m/z 291 (M+H).

EXAMPLE 8

Synthesis of Pyrimidine 11

$R_2$=Ph, $R_{3a}$=CHCHCH3, $R_{3d}$=H

A 2.0 M solution of PhMgCl in THF (13 mL, 25.7 mmol) was added to a –78° C. solution of dimethylketene dithioacetal 10 (5.7 g, 19.8 mmol) in 200 mL of THF. After 3 h at –78° C., saturated aqueous $NH_4Cl$ was added and the layers were separated. The aqueous layer was extracted with EtOAc and the combined organic extracts were washed with water and brine, dried over $Na_2SO_4$, concentrated, and purified by column chromatography eluting with 20% EtOAc in hexanes to give 4.9 g (77%) of the thioenol ether as a yellow solid. MS m/z 321 (M+H).

Solid guanidine hydrochloride (1.5 g, 15.3 mmol) was added to a solution of the thioenol ether (4.9 g, 15.3 mmol) and $K_2CO_3$ (2.6 g, 19.1 mmol) in 30 mL of DMF and the solution was heated to 80° C. After 6 h at 80° C., the solution was diluted with EtOAc and washed with water and brine. The organic layer was dried over $Na_2SO_4$, concentrated, and purified by column chromatography eluting with 40% EtOAc in hexanes to give 4.6 g (96%) of the pyrimidine regioisomers 11 as yellow solids. MS m/z 314 (M+H).

EXAMPLE 9

Synthesis of Aldehyde 13

$R_2$=Ph

Solid $MeSO_2NH_2$ (277 mg, 2.9 mmol) was added to a t-BuOH:$H_2O$ (1:1) solution (30 mL) of AD-mix-α (4.0 g). The resulting yellow solution was added to an EtOAc solution (15 mL) of the pyrimidine (910 mg, 2.9 mmol). After 3 days, solid sodium sulfite (4.4 g, 34.9 mmol) was added. After stirring for 1.5 h, the heterogeneous solution was diluted with EtOAc and the layers were separated. The aqueous phase was extracted with EtOAc and the combined extracts were washed with water and brine, dried over $Na_2SO_4$, concentrated, and purified by column chromatography eluting with 100% EtOAc to give 710 mg (70%) of the intermediate diol 12. MS m/z 348 (M+H).

Solid $HIO_4$-$2H_2O$ (933 mg, 4.1 mmol) was added to a 0° C. solution of diol 12 (710 mg, 2.1 mmol) in THF. After 1.5 h at 0° C., the solution was diluted with EtOAc and the organic phase was washed with saturated aqueous $NaHCO_3$, water, and brine. The organic layer was dried over $Na_2SO_4$ and concentrated to give 603 mg (98%) of aldehyde 13 as a yellow solid that was used without further purification. MS m/z 302 (M+H).

EXAMPLE 10

Synthesis of Amine 14 via Reductive Amination $R_{3a}$=N(—$CH_2CH_2OCH_2CH_2$—)

Solid $NaBH(OAc)_3$ (53 mg, 0.25 mmol) was added to a solution of aldehyde 13 (50 mg, 0.17 mmol), morpholine (0.034 mL, 0.34 mmol), and AcOH (0.014 mL, 0.25 mmol) in 1 mL of THF. After 3 d the solution was filtered and concentrated. The resulting material was dissolved in $CH_2Cl_2$ and washed with saturated aqueous $NaHCO_3$ and brine, dried over $Na_2SO_4$, concentrated, and purified by column chromatography eluting with 0-10% MeOH in $CH_2Cl_2$ to give 38 mg (60%) of the amine 14 as a yellow solid. MS m/z 373 (M+H). The product was dissolved in a minimum amount of $CH_2Cl_2$ and treated with 1.0 M HCl in ether to obtain the hydrochloride salt.

EXAMPLE 11

Cyclization to Form Dihydropyridine 16

$R_2$=2-furyl, $R_3$=H

To a solution of 3-dicyanovinylindan-1-one (4.06 g, 20.9 mmol) in 200 mL of ethanol was added 2-furaldehyde (3.01 g, 31.4 mmol) and 25 mL of conc. $NH_4OH$. The solution was heated to reflux for 2 h and allowed to cool to rt overnight. The mixture was concentrated in vacuo to remove ethanol. The residue was filtered and washed with water. The purple solid obtained was dried to yield 5.92 g (89%). MS m/z 290 ($M^+$+ 1).

EXAMPLE 12

Oxidation of Dihydropyridine 16 to Pyridine 17

$R_2$=2-furyl, $R_3$=H, $R_4$=$NH_2$, $R_5$=CN, X=O

To a refluxing solution of dihydropyridine 16 (5.92 g, 20.4 mmol) in acetic acid (100 mL) was added a solution of chromium (VI) oxide (2.05 g, 20.4 mmol) in 12 mL of water. After 10 minutes at reflux, the reaction was diluted with water until a precipitate started to form. The mixture was cooled to room temperature and filtered. The residue was washed with water to give 4.64 g (79%) of a brown solid. MS m/z 288 ($M^+$+1).

EXAMPLE 13

Reduction of Ketone 17 to Alcohol 18

To a 0° C. solution of ketone 17 (0.115 g, 0.40 mmol) in 12 mL of THF was added a 1.0 M LiAlH$_4$ solution in THF (0.40 mL, 0.40 mmol). The reaction was stirred at 0° C. for 1 h. The reaction was quenched by the addition of ethyl acetate (1.5 mL), water (1.5 mL), 10% aq. NaOH (1.5 mL), and saturated aq. NH$_4$Cl (3.0 mL). The mixture was extracted with ethyl acetate (3×35 mL), washed with brine, and dried over sodium sulfate. The remaining solution was concentrated to yield 0.083 g (72%) of a yellow solid. MS m/z 290 (M$^+$+1).

EXAMPLE 14

Hydrolysis of Nitrile 17 to Carboxylic Acid 19

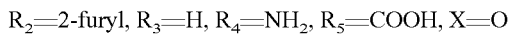

To a mixture of nitrile 17 (0.695 g, 2.42 mmol) and ethanol (30 mL) was added 5 mL of 35% aqueous sodium hydroxide. The resulting mixture was heated to reflux overnight. After cooling to rt, the solution was poured into water and acidified with 1 N HCl. The resulting precipitate was isolated by filtration and washed with water to yield 0.623 g (84%) of a brown solid. MS m/z 329 (M$^+$+23).

EXAMPLE 15

Synthesis of Carboxylic Ester 20 with Silver Carbonate

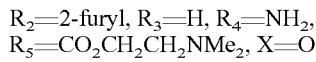

A suspension of carboxylic acid 19 (5.0 g, 16.3 mmol), silver carbonate (5.8 g, 21.2 mmol), and tetrabutylammonium iodide (1.5 g, 4.1 mmol) in 80 mL of DMF was heated to 90° C. After 1 h, the mixture was cooled to rt and 2-(dimethylamino)ethylchloride hydrochloride (2.4 g, 16.3 mmol) was added and the mixture was heated to 100° C. After 7 h, the reaction was filtered while hot, concentrated and purified by column chromatography eluting with 0-10% MeOH/CH$_2$Cl$_2$ to yield 0.160 g (3%) of a yellow solid. MS m/z 378 (M$^+$+1). The product was dissolved in a minimum of dichloromethane and treated with 1.0 M HCl in ether to obtain the hydrochloride salt.

EXAMPLE 16

Synthesis of Carboxylic Ester 20 with DEPC

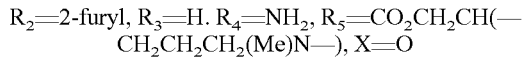

To a mixture of carboxylic acid 19 (0.40 g, 1.3 mmol) and (S)-1-methyl-2-pyrrolidinemethanol (0.50 mL, 3.9 mmol) in DMF (30 mL) was added 0.20 mL (1.3 mmol) of diethylphosphoryl cyanide and triethylamine (0.20 mL, 1.3 mmol). The reaction was stirred at 0° C. for one hour and then heated up to approximately 70° C. overnight. The reaction was then cooled to rt and diluted with ethyl acetate. The organic mixture was washed with saturated aqueous NaHCO$_3$, water, and brine. After being dried with sodium sulfate, the solution was concentrated. The residue was purified by column chromatography eluting with 10-100% ethyl acetate in hexane and then preparative TLC eluting with 2% MeOH in dichloromethane to yield 1.9 mg (0.4%) of a yellow solid. MS m/z 404 (M$^+$+1).

EXAMPLE 17

Synthesis of Carboxylic Amide 21 with DEPC

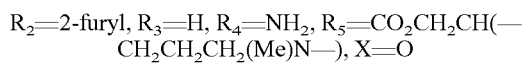

To a mixture of carboxylic acid 19 (0.25 g, 0.82 mmol) and N,N,N'-trimethylethylenediamine (0.14 mL, 1.08 mmol) in DMF (20 mL) was added 0.12 mL (0.82 mmol) of diethylphosphoryl cyanide and triethylamine (0.11 mL, 0.82 mmol). The reaction was stirred at 0° C. for one hour and then heated up to approximately 60° C. overnight. The reaction was then cooled to rt and diluted with ethyl acetate. The organic mixture was washed with saturated aqueous NaHCO$_3$, water, and brine. After being dried with magnesium sulfate, the solution was concentrated. The residue was purified by column chromatography eluting with 0-10% methanol in dichloromethane and then preparative TLC eluting with 1% MeOH in dichloromethane to yield 3.3 mg (10%) of a yellow solid. MS m/z 391 (M$^+$+1). The product was dissolved in a minimum of diethyl ether and treated with 1.0 M HCl in ether to obtain the hydrochloride salt.

EXAMPLE 18

Synthesis of Carboxylic Amide 21 with EDCl

A mixture of carboxylic acid 19 (0.300 g, 0.979 mmol), N-methylpiperazine (0.295 g, 2.94 mmol), 1-(3-dimethylaminopropyl)-3-ethylcarbodiimide hydrochloride (0.563 g, 2.94 mmol) 1-hydroxybenzotriazole hydrate (0.397 g, 2.94 mmol), triethylamine (0.298 g, 2.94 mmol) in DMF (8 mL) was stirred at rt overnight. The mixture was then diluted with water and extracted several times with ethyl acetate. The combined organics were washed twice with brine and then dried over sodium sulfate. The solution was concentrated and then purified by column chromatography to afford 0.092 g (2%) of solid. MS m/z 389 (M$^+$+1). The product was treated with 1.0 M HCl in ether to obtain the hydrochloride salt.

EXAMPLE 19

Synthesis of Carboxylic Ester 20 via a Dibromoalkane

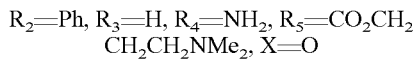

To a solution of carboxylic acid 19 (0.100 g, 0.32 mmol) in DMF (1.5 mL) was added 60% NaH dispersion in mineral oil (0.013 g, 0.32 mmol). After 10 min at rt, 1,3-dibromopropane (0.035 mL, 0.35 mmol) was added and the solution was stirred at rt for 17 h. After concentration, the residue was purified via column chromatography eluting with 40% ethyl acetate in hexanes to yield 0.014 g (9%) of a yellow solid. MS m/z 437 (M$^+$+1).

To a solution of the yellow solid (0.014 mg, 0.03 mmol) in a sealed tube was added a 40% aqueous solution of dimethylamine (0.5 mL, 3.0 mmol). The tube was heated to 75° C. for 2 h before concentrating. The residue was purified by column chromatography eluting with 0-10% methanol in dichloromethane to yield 0.009 g (70%) of a yellow solid. MS m/z 402 ($M^+$+1). The product was dissolved in a minimal amount of $CH_2Cl_2$ and treated with 1 N HCl in ether to obtain the hydrochloride salt.

Following the general synthetic procedures outlined above and in Examples 1-19, the compounds of Table 1 below were prepared.

TABLE 1

| No. | $R_2$ | $R_{3a}$ | $R_{3b}$ | $R_{3c}$ | $R_{3d}$ | $R_4$ | X | MS (M + 1) |
|---|---|---|---|---|---|---|---|---|
| 1 | 4-MeOPh | H | H | H | H | $NH_2$ | $CH_2$ | 290 |
| 2 | 4-MeOPh | H | H | H | H | $NH_2$ | CO | 304 |
| 3 | 2-furyl | H | H | H | H | $NH_2$ | CO | 264 |
| 4 | 2-furyl | H | H | H | H | $NH_2$ | $CH_2$ | 250 |
| 5 | 3-pyridyl | H | H | H | H | $NH_2$ | CO | 297 (+Na) |
| 6 | 4-pyridyl | H | H | H | H | $NH_2$ | CO | 275 |
| 7 | $C_3H_2NS$ (thiazol-2-yl) | H | H | H | H | $NH_2$ | CO | 281 |
| 8 | 4-$ClC_6H_4$ | H | H | H | H | $NH_2$ | CO | 308 |
| 9 | 3-$NO_2C_6H_4$ | H | H | H | H | $NH_2$ | CO | 319 |
| 10 | Ph | H | H | H | H | $NH_2$ | CO | 274 |
| 11 | 3-$MeOC_6H_4$ | H | H | H | H | $NH_2$ | CO | 304 |
| 12 | 2-$MeOC_6H_4$ | H | H | H | H | $NH_2$ | CO | 304 |
| 13 | 3-$HOC_6H_4$ | H | H | H | H | $NH_2$ | CO | 290 |
| 14 | 2-thiophenyl | H | H | H | H | $NH_2$ | CO | 302 |
| 15 | 3-thiophenyl | H | H | H | H | $NH_2$ | CO | 302 |
| 16 | 2-furyl | H | Br | H | H | $NH_2$ | CO | 342 |
| 17 | 2-furyl | OH | H | H | H | $NH_2$ | CO | 280 |
| 18 | $SCH_3$ | $NH_2$ | H | H | H | $NH_2$ | CO | 259 |
| 19 | 3-$FC_6H_4$ | H | H | H | H | $NCHNMe_2$ | CO | 347 |
| 20 | 2-furyl | $NH_2$ | H | H | H | $NH_2$ | CO | 279 |
| 21 | 2-furyl | H | H | H | $NH_2$ | $NH_2$ | CO | 279 |
| 22 | 2-furyl | H | $CF_3$ | H | H | $NH_2$ | CO | 332 |
| 23 | 2-furyl | H | H | $CF_3$ | H | $NH_2$ | CO | 332 |
| 24 | Ph | H | H | H | H | NHMe | CO | 288 |
| 25 | 2-furyl | H | Cl | Cl | H | $NH_2$ | CO | 332 |
| 26 | 2-furyl | Cl | H | H | Cl | $NH_2$ | CO | 332 |
| 27 | Ph | H | H | H | H | $N(CH_2)_2NEt_2$ | CO | 373 |
| 28 | 3,4-$F_2C_6H_3$ | H | H | H | H | $NH_2$ | CO | 310 |
| 29 | 3,5-$F_2C_6H_3$ | H | H | H | H | $NH_2$ | CO | 310 |
| 30 | $C_6H_6HO$ (6-methoxypyridin-3-yl) | H | H | H | H | $NH_2$ | CO | 305 |
| 31 | 3,4,5-$F_3C_2H_2$ | H | H | H | H | $NH_2$ | CO | 340 (M + Na) |

TABLE 1-continued

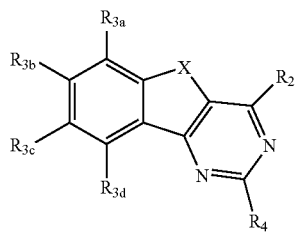

| No. | R$_2$ | R$_{3a}$ | R$_{3b}$ | R$_{3c}$ | R$_{3d}$ | R$_4$ | X | MS (M + 1) |
|---|---|---|---|---|---|---|---|---|
| 32 | Ph | [structure] C$_3$H$_7$O$_2$ (HO, OH with two methyls) | H | H | H | NH$_2$ | CO | 348 |
| 33 | Ph | H | H | H | [structure] C$_3$H$_7$O$_2$ (HO, OH with two methyls) | NH$_2$ | CO | 348 |
| 34 | [structure: 1-propyl-2-pyridinone-5-yl] C$_8$H$_{10}$NO | H | H | H | H | NH$_2$ | CO | 333 |
| 35 | 2-furyl | H | H | Br | H | NH$_2$ | CO | 342/344 |
| 36 | 2-furyl | H | H | H | F | NH$_2$ | CO | 282 |
| 37 | 2-furyl | MeO | H | H | H | NH$_2$ | CO | 294 |
| 38 | 4-FC$_6$H$_4$ | H | H | H | H | NH$_2$ | CO | 292 |
| 39 | 3-FC$_6$H$_4$ | H | H | H | H | NH$_2$ | CO | 292 |
| 40 | SO$_2$Me | H | H | H | H | NH$_2$ | CO | 298 |
| 41 | Sme | H | H | H | H | NH$_2$ | CO | 266 |
| 42 | Ome | H | H | H | H | NH$_2$ | CO | 477 (2M + Na) |
| 43 | NHPh | H | H | H | H | NH$_2$ | CO | 289 |
| 44 | 3-furyl | H | H | H | H | NH$_2$ | CO | 264 |
| 45 | 5-methyl-2-furyl | H | H | H | H | NH$_2$ | CO | 278 |
| 46 | 2-furyl | OCH$_2$CH$_2$NHCO$_2$tBu | H | H | H | NH$_2$ | CO | 437 |
| 47 | Ph | H | H | H | H | Me | CO | 297 |
| 48 | Ph | H | H | H | H | OMe | CO | 291 |
| 49 | Ph | CH$_2$NMeCH$_2$CH$_2$NMe$_2$ | H | H | H | NH$_2$ | CO | 388 |
| 50 | Ph | [structure: CH$_2$-N-methylpiperazine] C$_6$H$_{13}$N$_2$ | H | H | H | NH$_2$ | CO | 386 |
| 51 | Ph | [structure: CH$_2$-morpholine] C$_5$H$_{10}$NO | H | H | H | NH$_2$ | CO | 373 |

TABLE 1-continued
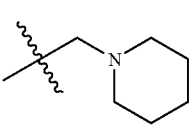
| No. | $R_2$ | $R_{3a}$ | $R_{3b}$ | $R_{3c}$ | $R_{3d}$ | $R_4$ | X | MS (M + 1) |
|---|---|---|---|---|---|---|---|---|
| 52 | Ph | $CH_2NEt_2$ | H | H | H | $NH_2$ | CO | 359 |
| 53 | Ph | 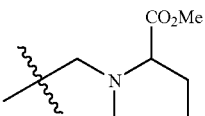<br>$C_6H_{12}N$ | H | H | H | $NH_2$ | CO | 371 |
| 54 | Ph | 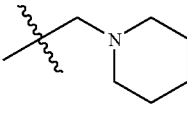<br>$C_8H_{14}NO_2$ | H | H | H | $NH_2$ | CO | 429 |
| 55 | Ph | 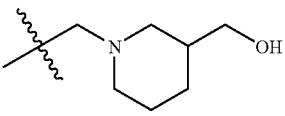<br>$C_9H_{16}NO_2$ | H | H | H | $NH_2$ | CO | 443 |
| 56 | Ph | $CH_2NMeCH_2CO_2Me$ | H | H | H | $NH_2$ | CO | 389 |
| 57 | Ph | 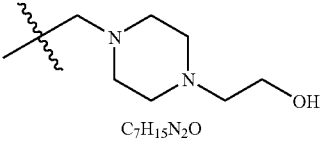<br>$C_7H_{14}NO416$ | H | H | H | $NH_2$ | CO | 401 |
| 58 | Ph | 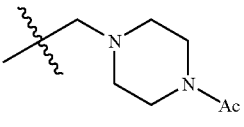<br>$C_7H_{15}N_2O$ | H | H | H | $NH_2$ | CO | 416 |
| 59 | Ph | 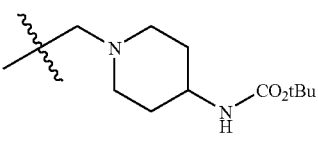<br>$C_7H_{13}N_2O$ | H | H | H | $NH_2$ | CO | 414 |
| 60 | Ph | <br>$C_{11}H_{21}N_2O_2$ | H | H | H | $NH_2$ | CO | 486 |

TABLE 1-continued

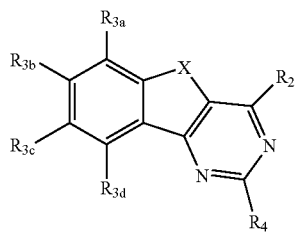

| No. | R$_2$ | R$_{3a}$ | R$_{3b}$ | R$_{3c}$ | R$_{3d}$ | R$_4$ | X | MS (M + 1) |
|---|---|---|---|---|---|---|---|---|
| 61 | Ph | ≈N(Et)CH$_2$-(4-pyridyl), C$_9$H$_{13}$N$_2$ | H | H | H | NH$_2$ | CO | 422 |
| 62 | Ph | ≈N(Me)CH$_2$-(2-furyl), C$_7$H$_{10}$NO | H | H | H | NH$_2$ | CO | 397 |

TABLE 2

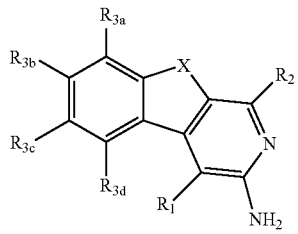

| No. | X | R$_2$ | R$_{3a}$ | R$_{3b}$ | R$_{3c}$ | R$_{3d}$ | R$_1$ | MS (M + 1) |
|---|---|---|---|---|---|---|---|---|
| 63 | CO | 2-furyl | H | H | H | H | CN | 288 |
| 64 | CO | Ph | H | H | H | H | CN | 298 |
| 65 | CO | Ph | H | H | H | H | COOH | 315 (M − 1) |
| 66 | CO | 3-furyl | H | H | H | H | CN | 288 |
| 67 | CO | 3-FC$_6$H$_4$ | H | H | H | H | CN | 316 |
| 68 | CO | 3-pyridyl | H | H | H | H | CN | 299 |
| 69 | CO | 2-furyl | H | H | H | H | COOH | 305 (M − 1) |
| 70 | CO | 2-furyl | H | H | H | H | CO$_2$CH$_2$CH$_2$NMe$_2$ | 378 |
| 71 | CO | 4-FC$_6$H$_4$ | H | H | H | H | CN | 316 |
| 72 | CO | 2-thiophenyl | H | H | H | H | CN | 304 |
| 73 | CO | 3-thiophenyl | H | H | H | H | CN | 304 |
| 74 | CO | 3-MeOC$_6$H$_4$ | H | H | H | H | CN | 328 |
| 75 | CO | 2-imidazolyl | H | H | H | H | CN | 288 |
| 76 | CO | 2-furyl | H | H | H | H | CONHCH$_2$CH$_2$NMe$_2$ | 377 |
| 77 | CO | 2-furyl | H | H | H | H | CONMeCH$_2$OH$_2$NMe$_2$ | 391 |
| 78 | CO | 2-furyl | H | H | H | H | CONHCHMeCH$_2$NMe$_2$ | 391 |
| 79 | CO | 2-furyl | F | F | F | F | CN | 358 (M − 1) |

TABLE 2-continued
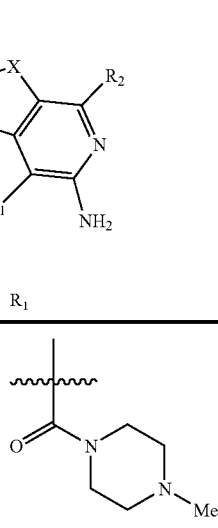
| No. | X | R₂ | R₃ₐ | R₃ᵦ | R₃c | R₃d | R₁ | MS (M + 1) |
|---|---|---|---|---|---|---|---|---|
| 80 | CO | 2-furyl | H | H | H | H | 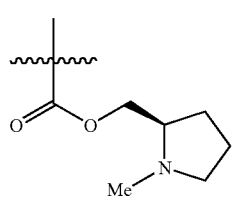<br>$C_6H_4NO_2C_6H_{11}N_2O$ | 389 |
| 81 | CO | Ph | H | H | H | H | $CO_2CH_2CH_2NMe_2$ | 388 |
| 82 | CO | 2-furyl | H | H | H | H | 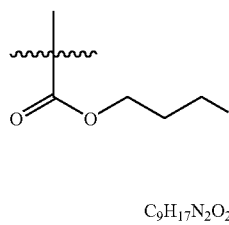<br>$C_7H_{12}NO_2$ | 404 |
| 83 | CO | Ph | H | H | H | H | 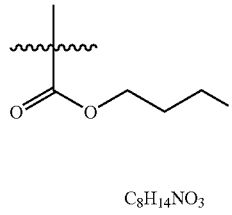<br>$C_9H_{17}N_2O_2$ | 457 |
| 84 | CO | Ph | H | H | H | H | 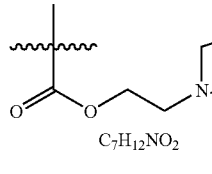<br>$C_8H_{14}NO_3$ | 444 |
| 85 | CO | Et | H | H | H | H | CN | 250 |
| 86 | CO | i-Bu | H | H | H | H | CN | 278 |
| 87 | CO | Ph | H | H | H | H | $CO_2CH_2CH_2CH_2NMe_2$ | 402 |
| 88 | CO | Ph | H | H | H | H | <br>$C_7H_{12}NO_2$ | 414 |
| 89 | CHOH | 2-furyl | H | H | H | H | CN | 290 |

TABLE 2-continued

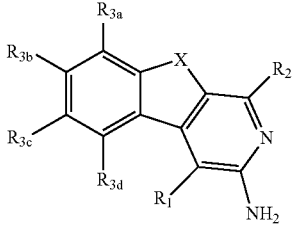

| No. | X | R$_2$ | R$_{3a}$ | R$_{3b}$ | R$_{3c}$ | R$_{3d}$ | R$_1$ | MS (M + 1) |
|---|---|---|---|---|---|---|---|---|
| 90 | CO | Ph | H | H | H | H | 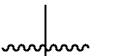 C$_7$H$_{12}$NO$_2$ | 414 |
| 91 | CO | Ph | H | H | H | H | 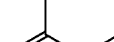 C$_7$H$_{12}$NO$_2$ | 430 |
| 92 | CO | Ph | H | H | H | H | CO$_2$CH$_2$CHMeCH$_2$NMe$_2$ | 416 |
| 93 | CO | 3-thiophenyl | H | H | H | H | CO$_2$CH$_2$CH$_2$NMe$_2$ | 394 |
| 94 | CO | CH$_2$CH$_2$CHCH$_2$ | H | H | H | H | CN | 276 |
| 95 | CO | c-Hex | H | H | H | H | CN | 302 |
| 96 | CO | 2-furyl | H | H | H | H | (S)-CO$_2$CHMeCH$_2$NMe$_2$ | (M − 1) 392 |

III. Biological Assays and Activity

Ligand Binding Assay for Adenosine A2a Receptor

Ligand binding assay of adenosine A2a receptor was performed using plasma membrane of HEK293 cells containing human A2a adenosine receptor (PerkinElmer, RB-HA2a) and radioligand [$^3$H]CGS21680 (PerkinElmer, NET1021). Assay was set up in 96-well polypropylene plate in total volume of 200 µL by sequentially adding 20 µL 1:20 diluted membrane, 130 µL assay buffer (50 mM Tris.HCl, pH7.4 10 mM MgCl$_2$, 1 mM EDTA) containing [$^3$H] CGS21680, 50 µL diluted compound (4×) or vehicle control in assay buffer. Nonspecific binding was determined by 80 mM NECA. Reaction was carried out at room temperature for 2 hours before filtering through 96-well GF/C filter plate pre-soaked in 50 mM Tris.HCl, pH7.4 containing 0.3% polyethylenimine. Plates were then washed 5 times with cold 50 mM Tris.HCl, pH7.4, dried and sealed at the bottom. Microscintillation fluid 30 µl was added to each well and the top sealed. Plates were counted on Packard Topcount for [$^3$H]. Data was analyzed in Microsoft Excel and GraphPad Prism programs. (Varani, K.; Gessi, S.; Dalpiaz, A.; Borea, P. A. British Journal of Pharmacology, 1996, 117, 1693)

Adenosine A2a Receptor Functional Assay

CHO-K1 cells overexpressing human adenosine A2a receptors and containing cAMP-inducible beta-galactosidase reporter gene were seeded at 40-50 K/well into 96-well tissue culture plates and cultured for two days. On assay day, cells were washed once with 200 µL assay medium (F-12 nutrient mixture/0.1% BSA). For agonist assay, adenosine A2a receptor agonist NECA was subsequently added and cell incubated at 37° C., 5% CO$_2$ for 5 hrs before stopping reaction. In the case of antagonist assay, cells were incubated with antagonists for 5 minutes at R.T. followed by addition of 50 nM NECA. Cells were then incubated at 37° C., 5% CO$_2$ for 5 hrs before stopping experiments by washing cells with PBS twice. 50 µL 1× lysis buffer (Promega, 5× stock solution, needs to be diluted to 1× before use) was added to each well and plates frozen at −20° C. For β-galactosidase enzyme calorimetric assay, plates were thawed out at room temperature and 50 µL 2× assay buffer (Promega) added to each well. Color was allowed to develop at 37° C. for 1 h or until reasonable signal appeared. Reaction was then stopped with 150 µL 1 M sodium carbonate. Plates were counted at 405 nm on Vmax Machine (Molecular Devices). Data was analyzed in Microsoft Excel and GraphPad Prism programs. (Chen, W. B.; Shields, T. S.; Cone, R. D. Analytical Biochemistry, 1995, 226, 349; Stiles, G. Journal of Biological Chemistry, 1992, 267, 6451)

Haloperidol-Induced Catalepsy Study in C57bl/6 Mice

Mature male C57bl/6 mice (9-12 week old from ACE) were housed two per cage in a rodent room. Room temperature was maintained at 64-79 degrees and humidity at 30-70% and room lighting at 12 hrs light/12 hrs dark cycle. On the study day, mice were transferred to the study room. The mice were injected subcutaneously with haloperidol (Sigma H1512, 1.0 mg/ml made in 0.3% tartaric acid, then diluted to 0.2 mg/ml with saline) or vehicle at 1.5 mg/kg, 7.5 ml/kg. The mice were then placed in their home cages with access to water and food. 30 minutes later, the mice were orally dosed with vehicle (0.3% Tween 80 in saline) or compounds at 10 mg/kg, 10 ml/kg (compounds, 1 mg/ml, made in 0.3% Tween 80 in saline, sonicated to obtain a uniform suspension). The mice were then placed in their home cages with access to water and food. 1 hour after oral dose, the catalepsy test was performed. A vertical metal-wire grid (1.0 cm squares) was used for the test. The mice were placed on the grid and given a few seconds to settle down and their immobility time was recorded until the mice moved their back paw(s). The mice were removed gently from the grid and put back on the grid and their immobility time was counted again. The measurement was repeated three times. The average of three measurements was used for data analysis.

Compound 70 showed 87% inhibition and compound 3 showed 90% inhibition of haloperidol-induced catalepsy when orally dosed at 10 mg/kg.

TABLE 5

| No. | A2a binding | A2a antagonist function | A1 antagonist function |
|---|---|---|---|
| 1 | 44.64 | 233.7 | 52.98 |
| 2 | 2.032 | 6.868 | 5.32 |
| 3 | 0.26 | 0.0066 | 0.288 |
| 4 | 0.885 | 2.63 | 15.57 |
| 5 | 5.355 | 9.64 | 27.1 |
| 6 | 3.9 | 4.56 | 16.44 |
| 7 | 0.26 | 0.49 | 6.89 |
| 8 | 58.41 | 5.5 | 11.59 |
| 9 | 20.82 | 4.85 | 7.69 |
| 10 | 6.1 | 0.109 | 1.2 |
| 11 | 8.85 | 1.63 | 2.47 |
| 12 | 33.49 | 32.52 | 172.3 |
| 13 | 5.16 | 35.59 | 10.35 |
| 14 | 2.19 | 0.59 | 3.19 |
| 15 | 3.23 | 0.258 | 3.46 |
| 16 | 1.75 | 0.169 | 5.22 |
| 17 | 6.3 | 67.14 | 111.29 |
| 18 | 317.95 | >3000 | 188.99 |
| 19 | 110.73 | 20.88 | 21.64 |
| 20 | 0.05 | 0.126 | 0.91 |
| 21 | 0.376 | 0.053 | 3.51 |
| 22 | 14.16 | 0.055 | 2.75 |
| 23 | 13.58 | 0.55 | 1.47 |
| 24 | 30.32 | >3000 | 5.99 |
| 25 | 172.85 | 5.69 | 17.44 |
| 26 | 34.57 | 0.88 | 3.13 |
| 27 | 146.84 | 68.28 | >1000 |
| 28 | 48.9 | 3.53 | 5.86 |
| 29 | 20.95 | 1.42 | 4.27 |
| 30 | 31.55 | 10.15 | 4.05 |
| 31 | 140.68 | 15.22 | 17.5 |
| 32 | 3.55 | 0.634 | 9.89 |
| 33 | 0.175 | 0.34 | 0.021 |
| 34 | 560.13 | | |
| 35 | 3.49 | 0.265 | 7.09 |
| 36 | 4.37 | 0.052 | 2.52 |
| 37 | 2.86 | 0.143 | 3.07 |
| 38 | 2.34 | 0.956 | 9.44 |
| 39 | 4.92 | 0.926 | 2.31 |
| 40 | 2720.46 | | |
| 41 | 88.01 | 575.43 | >3000 |
| 42 | 118.2 | 782.18 | >10000 |
| 43 | 39.9 | 3.68 | 2.34 |
| 44 | 3.93 | 0.208 | 7.4 |
| 45 | 4.013 | 0.005 | 0.016 |
| 46 | 60.56 | 490.14 | 32.54 |
| 47 | 1076.76 | | |
| 48 | 470.84 | >1000 | >1000 |
| 49 | 51.12 | 40.13 | 119.03 |
| 50 | 80.15 | 11.31 | 94.24 |
| 51 | 36.81 | 3.26 | 32.92 |
| 52 | 94.41 | 18.33 | 107.17 |
| 53 | 64.15 | 14.25 | 40.82 |
| 54 | 40.79 | 3.19 | 19.56 |
| 55 | 32.82 | 5.84 | 19.86 |
| 56 | 25.72 | 6.81 | 25.76 |
| 57 | 34.02 | 15.93 | 39.29 |
| 58 | 30.65 | 11.65 | 60.99 |
| 59 | 40.79 | 7.94 | 34.11 |
| 60 | 34.29 | | |
| 61 | 29.83 | | |
| 62 | 58.39 | | |
| 63 | 0.59 | 0.0002 | 0.18 |
| 64 | 13.09 | 0.138 | 4.61 |
| 65 | 574.71 | 244.96 | 163.36 |
| 66 | 4.21 | 0.069 | 15.59 |
| 67 | 13.4 | 0.618 | 4.37 |
| 68 | 7.59 | 0.73 | 34.84 |
| 69 | 2261 | 90.16 | >1000 |
| 70 | 9.89 | 0.44 | 20.13 |
| 71 | 17.24 | 3.39 | 2.42 |
| 72 | 12.64 | 2.54 | 6.24 |
| 73 | 4.925 | 0.06 | 9.7 |
| 74 | 14.67 | 5.7 | 7.28 |
| 75 | 23.72 | 1.51 | 78.33 |
| 76 | 33.03 | 22.13 | >500 |
| 77 | 6.254 | 0.68 | >500 |
| 78 | 17.65 | 1.58 | >500 |
| 79 | 8.03 | 12.48 | >1000 |
| 80 | 69.08 | 15.86 | 55.99 |
| 81 | 228.7 | 29.03 | 33.63 |
| 82 | 20.24 | 1.36 | 29.58 |
| 83 | 200.06 | 74.87 | 117.05 |
| 84 | 173.98 | 24.71 | 27.42 |
| 85 | 507.72 | | |
| 86 | 244.07 | >1000 | 39.26 |
| 87 | 98.93 | 39.45 | >300 |
| 88 | 129.6 | 48.87 | >300 |
| 89 | 5.85 | 1.12 | 11.16 |
| 90 | 202.17 | 57.7 | >300 |
| 91 | 208.32 | 22.07 | 14.67 |
| 92 | 38.82 | 13.9 | 32.88 |
| 93 | 64.05 | 23.57 | 104.31 |
| 94 | 49.55 | >1000 | 35.99 |
| 95 | 338.13 | >1000 | 110.22 |
| 96 | 48.55 | 10.08 | 52.45 |

What is claimed is:

1. A compound having the structure of Formula I

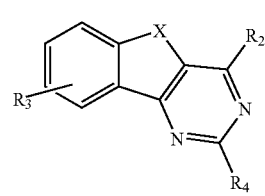

Formula I or a pharmaceutically acceptable salt thereof,
wherein
(a) $R_2$ is selected from, optionally substituted aryl,
(b) $R_3$ is from one to four groups independently selected from the group consisting of: hydrogen, halo, $C_{1-8}$ straight or branched chain alkyl, arylalkyl, $C_{3-7}$ cycloalkyl, $C_{1-8}$ alkoxy, cyano, $C_{1-4}$ carboalkoxy, trifluoromethyl, $C_{1-8}$ alkylsulfonyl, halogen, nitro, hydroxy, trifluoromethoxy, $C_{1-8}$ carboxylate, aryl and —$NR_{11}R_{12}$, wherein;
$R_{11}$ and $R_{12}$ are independently selected from H, $C_{1-8}$ straight or branched chain alkyl, arylalkyl, $C_{3-7}$ cycloalkyl, carboxyalkyl and aryl, and, -$NR_{13}COR_{14}$, wherein;
$R_{13}$ is selected from hydrogen or alkyl and $R_{14}$ is selected from hydrogen, alkyl, substituted alkyl, $C_{1-3}$ alkoxyl, carboxyalkyl, aryl, arylalkyl, $R_{15}R_{16}N(CH_2)_p$—, or $R_{15}R_{16}NCO(CH_2)_p$—, Wherein;
$R_{15}$ and $R_{16}$ are independently selected from H, OH, alkyl, and alkoxy, and p is an integer from 1-6, wherein;
the alkyl group may be substituted with carboxyl, alkyl, aryl, substituted aryl hydroxamic acid, sulfonamide, sulfonyl, hydroxy, thiol, alkoxy or arylalkyl;

(c) $R_4$ is amino, (d) X is C=O.

2. The compound of claim 1, formula I, wherein $R_3$ is $C_{1-8}$ alkoxy.

3. The compound of claim 1, formula I, wherein $R_2$ is phenyl.

4. A pharmaceutical composition comprising the compound of claim 1 and a pharmaceutically acceptable carrier.

* * * * *